United States Patent
Katz

(10) Patent No.: US 11,213,494 B2
(45) Date of Patent: Jan. 4, 2022

(54) COMPOSITIONS AND METHODS FOR THE TREATMENT OF PERVASIVE DEVELOPMENT DISORDERS

(71) Applicant: Case Western Reserve University, Cleveland, OH (US)

(72) Inventor: David M. Katz, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/469,024

(22) Filed: Mar. 24, 2017

(65) Prior Publication Data
US 2018/0008559 A1 Jan. 11, 2018

Related U.S. Application Data

(60) Provisional application No. 62/312,749, filed on Mar. 24, 2016.

(51) Int. Cl.
| | |
|---|---|
| *A61K 31/135* | (2006.01) |
| *A61P 25/00* | (2006.01) |
| *A61K 45/06* | (2006.01) |
| *A61K 31/498* | (2006.01) |
| *A61K 31/453* | (2006.01) |
| *A61K 31/5365* | (2006.01) |

(52) U.S. Cl.
CPC ........ *A61K 31/135* (2013.01); *A61K 31/453* (2013.01); *A61K 31/498* (2013.01); *A61K 31/5365* (2013.01); *A61K 45/06* (2013.01); *A61P 25/00* (2018.01)

(58) Field of Classification Search
CPC ........ A61P 25/00; A61K 31/135; A61K 45/06
See application file for complete search history.

(56) References Cited

U.S. PATENT DOCUMENTS

2005/0148673 A1* 7/2005 Harbut ................. A61K 31/137
514/650

FOREIGN PATENT DOCUMENTS

| WO | WO 2013/163455 | * 10/2013 |
| WO | WO 2014/169272 | * 10/2014 |

OTHER PUBLICATIONS

Schmid et al. A TrkB small molecule partial agonist rescues TrkB phosphorylation deficits and improves respiratory function in a mouse model of Rett syndrome. The Journal of Neuroscience, Feb. 1, 2012, 32(5): 1803-1810.*
Devarakonda et al. (Paediatric Anaesthesia, 2009, 19(6): 625-627).*
Patrizi et al., "Chronic Administration of the N-Methyl-D-Aspartate Receptor Antagonist Ketamine Improves Rett Syndrome Phenotype," Biol. Psychiatry May 1, 2016 (Epub. Aug. 24, 2015);79(9):755-64, with supplemental materials. PMID: 26410354. (Year: 2015).*

* cited by examiner

*Primary Examiner* — Theodore R. Howell
(74) *Attorney, Agent, or Firm* — Tarolli, Sundheim, Covell & Tummino LLP

(57) ABSTRACT

A method of treating a pervasive development disorder in a subject includes administering to the subject a therapeutically effective amount of an NMDAR antagonist, with an intermittent dosing regimen.

8 Claims, 14 Drawing Sheets

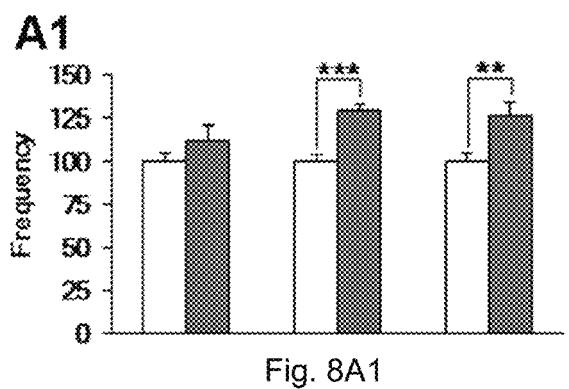
Fig. 8A1
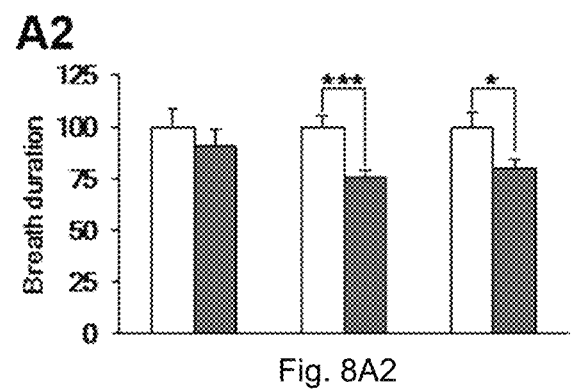
Fig. 8A2
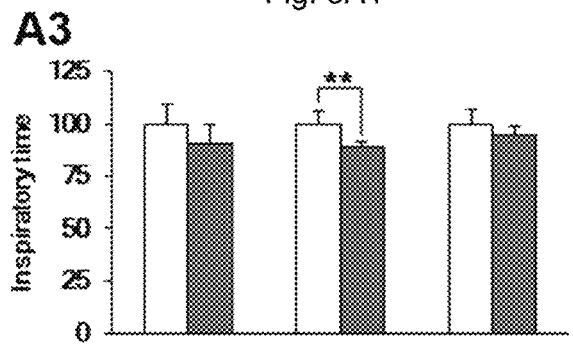
Fig. 8A3
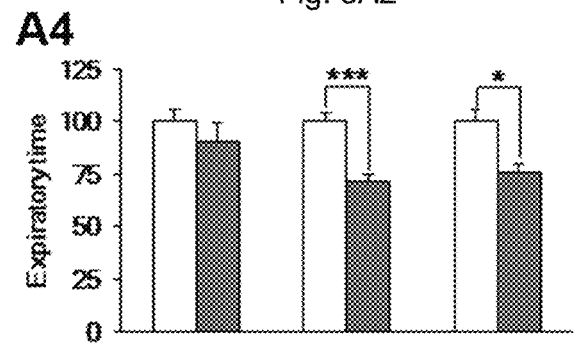
Fig. 8A4
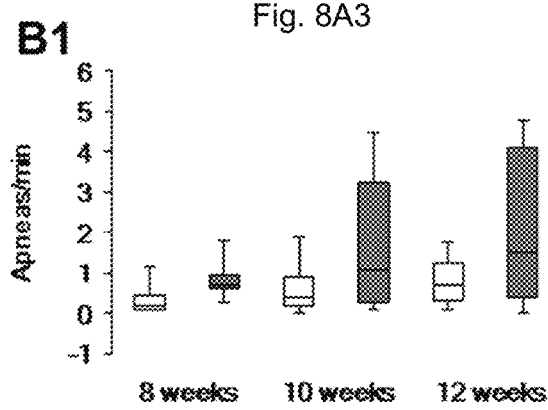
Fig. 8B1
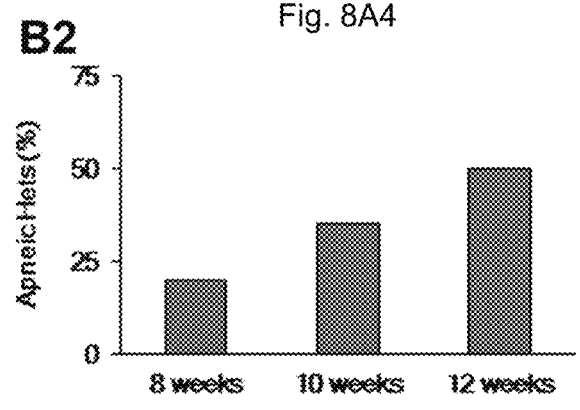
Fig. 8B2

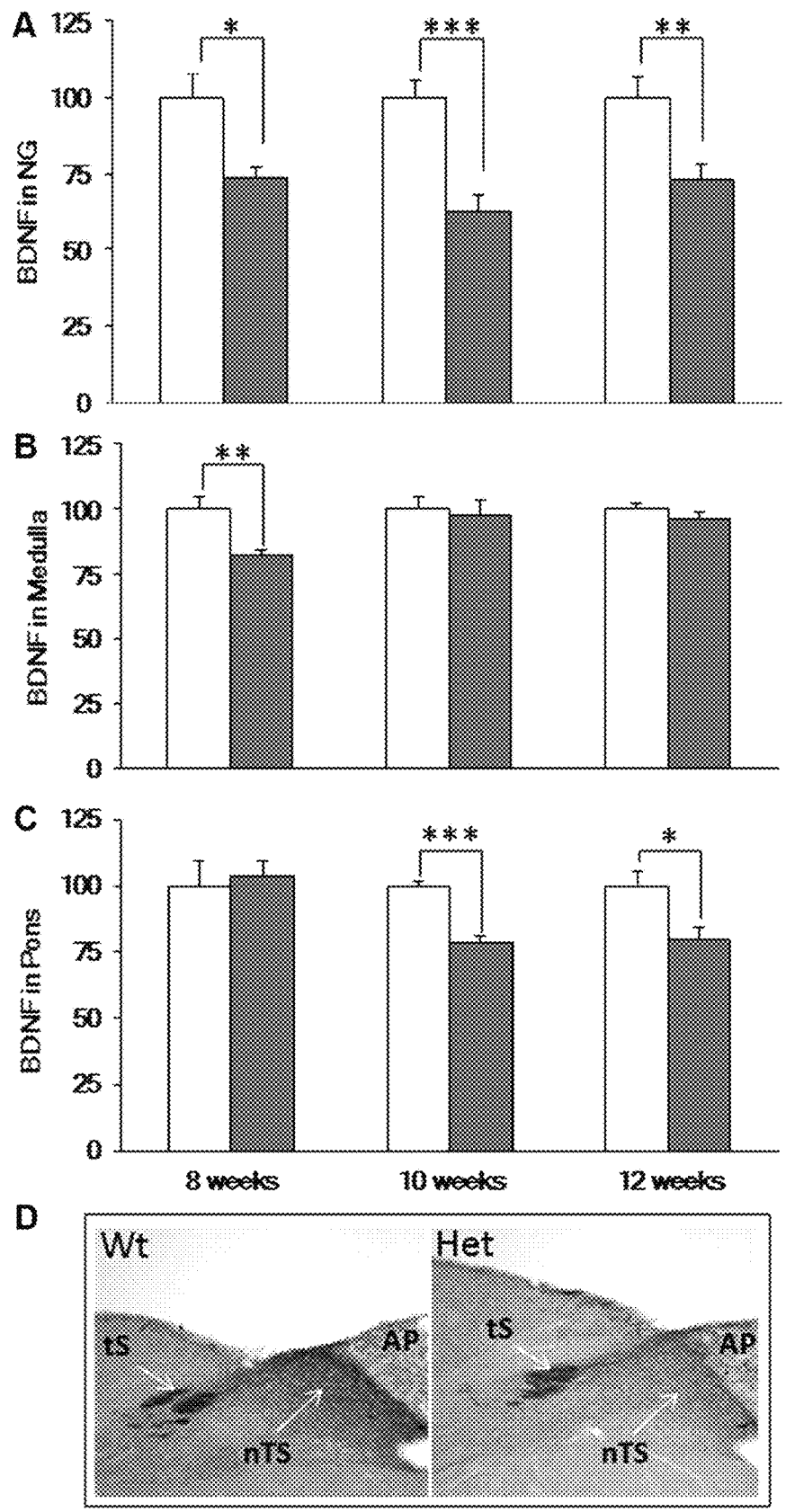
Figs. 9A-D

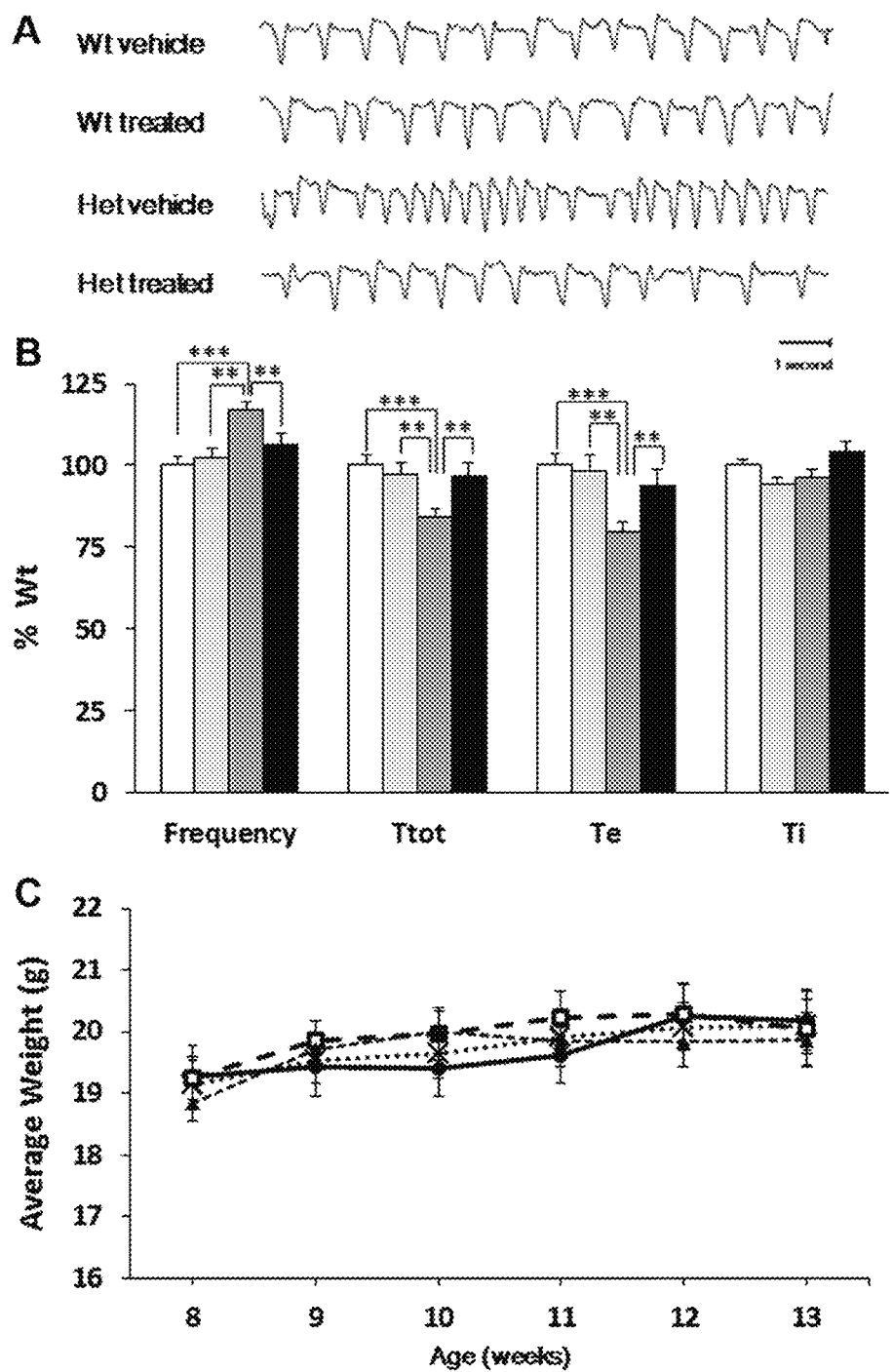
Figs. 10A-C

COMPOSITIONS AND METHODS FOR THE TREATMENT OF PERVASIVE DEVELOPMENT DISORDERS

RELATED APPLICATION

This application is claims priority to U.S. Provisional Application Ser. No. 62/312,749, filed Mar. 24, 2016, the subject matter of which is incorporated herein by reference in its entirety.

GOVERNMENT FUNDING

This invention was made with government support under Grant No. NS057398 awarded by The National Institutes of Health/NINDS, Autism Speaks Foundation. The United States government has certain rights to the invention.

FIELD OF THE INVENTION

The present application relates to compositions, methods and dosing regimens used for treating pervasive development disorders, and particularly relates to compositions, methods, and dosing regimens using NMDA receptor antagonists.

BACKGROUND

Pervasive development disorders refer to a group of disorders characterized by delays in the development of multiple basic functions including socialization and communication. Pervasive developmental disorders include autism, Asperger syndrome, pervasive developmental disorder not otherwise specified (PDD-NOS), childhood disintegrative disorder, and Rett syndrome.

Rett Syndrome (RTT) is a pervasive developmental disorder that shares several clinical signs with autism but has an unrelated cause. RTT is caused by loss-of-function mutations in the gene encoding the methyl-CpG binding protein 2 (MeCP2), a transcriptional regulatory protein. After a period of apparently normal early postnatal development, RTT patients develop a spectrum of symptoms that generally includes loss of acquired speech, head growth deceleration, autistic behaviors, motor, respiratory and autonomic dysfunction and increased risk of seizures. Inactivation of Mepc2 at any age leads to RTT-like symptoms indicating that MeCP2 protein is required across the lifespan for normal brain function.

However, loss of MeCP2 in RTT patients and mouse models is not associated with neuronal cell death or axonal degeneration, although neurons are smaller, more densely packed than normal and exhibit reduced dendritic arborizations, spine density and synapse number. In addition, Mecp2 mutant mice exhibit defects in neuronal and synaptic function, including alterations in excitatory/inhibitory (E/I) balance. These microcircuit abnormalities are accompanied by altered expression of neurotransmitters, neurotransmitter synthesizing enzymes, receptors and transporters, as well as molecules required for synapse development.

SUMMARY

Embodiments described herein relate to compositions, methods, and dosing regimens for treating pervasive development disorders, such as Rett Syndrome, in a subject in need thereof. The method includes administering to the subject a subanesthetic dose of an NMDAR antagonist effective to alleviate at least one symptom associated with the pervasive development disorder in an intermittent dosing regimen.

In some embodiments, the intermittent dosing regimen can include administering the subanesthetic dose of the NMDAR antagonist on a dosing interval effective to alleviate at least one symptom associated with the pervasive development disorder. The dosing interval of the NMDAR antagonist is then stopped or withheld once the at least one symptom has been at least partially or substantially alleviated. The dosing interval of the NMDAR antagonist is then re-administered to the subject upon recurrence of the at least one symptom. For example, the subanesthetic dose of the NMDAR antagonist can be initially administered to the subject over a multi-day dosing interval. Administration of the NMDAR antagonist can be stopped once the at least one symptom is at least partially or substantially alleviated. The dosing interval of the NMDAR antagonist can then be resumed to the subject upon recurrence of the at least one symptom for time period effective to alleviate the at least one symptom. The dosing regimen can be repeated as necessary to alleviate the at least one symptom.

In some embodiments, the subanesthetic dose of the NMDAR antagonist can be administered to the subject at dosing intervals of at least 12 hours. For example, the dosing interval is at least 12 hours, 24 hours, 36 hours, 48 hours, 72 hours, 96 hours, 1 day, 2 days, 3 days, 4 days, 5 days, 6 days, 7 days, 8 days, 9 days, 10 days, 11 days, 12 days, 13 days, 14 days, 90 days, 1 week, 2 weeks, 3 weeks, 4 weeks, or longer, or any combination or increment thereof.

In some embodiments, the at least one symptom can include a motor, respiratory and/or autonomic dysfunction associated with the pervasive development disorder. For example, the at least one symptom can include loss of normal movement and coordination, loss of communication ability, abnormal hand movements, such as hand wringing, squeezing, clapping, tapping, or rubbing, unusual eye movements, such as intense staring, blinking, crossed eyes or closing one eye at a time, breathing or respiratory problems, such as hyperventilation and apneic breathing, agitation and irritability, cognitive disabilities, seizures, irregular heartbeat, pain, as well as problems with chewing and swallowing and teeth grinding.

In some embodiments, the therapeutically effective amount of the subanesthetic dose of the NMDAR antagonist is an amount effective to ameliorate biochemical and functional abnormalities associated with loss-of-function mutations of the gene encoding methyl-CpG binding protein 2 (MeCP2) in the subject.

In some embodiments, the NMDAR antagonist is selected from the group consisting of Amantadine, AZD6765, Dextrallorphan, Dextromethorphan, Dextrorphan, Diphenidine, Dizocilpine (MK-801), Ethanol, Eticyclidine, Gacyclidine, Ibogaine, Memantine, Methoxetamine, Nitrous oxide, Phencyclidine, Rolicyclidine, Tenocyclidine, Methoxydine, Tiletamine, Xenon, Neramexane, Eliprodil, Etoxadrol, Dexoxadrol, WMS-2539, NEFA, Delucemine, 8A-PDHQ, Aptiganel, HU-211, Remacemide, Rhynchophylline, Ketamine, 1-Aminocyclopropanecarboxylic acid (ACPC), 7-Chlorokynurenate' DCKA (5,7-dichlorokynurenic acid), Kynurenic acid, Lacosamide, L-phenylalanine, Neurotransmitters, Psychedelics, Long-term potentiation, and NMDA. In some embodiments, the NMDAR antagonist is Remacemide.

In some embodiments, the method further includes administering to the subject a therapeutically effective amount of a TrkB agonist. The TrkB agonist can be selected from the group consisting of a small molecule, protein and an antibody.

In other embodiments, the method can further include administering to the subject an agent that modulates BDNF levels in the subject. The agent can be an ampakine. The ampakine can include an allosteric modulator of the AMPA-receptor.

In a particular aspect, the NMDAR antagonist can include ketamine or Remacemide and the TrkB agonist can include N,N',N"'Tris(2-hydroxyethyl)-1,3,5-benzenetricarboxamide (LM22A-4).

Other aspects described herein relate to a pharmaceutical composition for the treatment of Rett syndrome. The composition includes a therapeutically effective amount of an NMDAR antagonist, a therapeutically effective amount of a TrkB agonist, optionally an agent that modulates BDNF levels, and a pharmaceutically acceptable diluent or carrier. The therapeutically effective amounts of an NMDAR antagonist, a TrkB agonist, and optionally an agent that modulates BDNF levels can be an amount effective to ameliorate biochemical and functional abnormalities associated with pervasive development disorder, e.g., Rett syndrome. In some aspects, the therapeutically effective amount of an NMDAR antagonist can be sub-anesthetic.

In some aspects, the NMDAR antagonist can be selected from the group consisting of Amantadine, AZD6765, Dextrallorphan, Dextromethorphan, Dextrorphan, Diphenidine, Dizocilpine (MK-801), Ethanol, Eticyclidine, Gacyclidine, Ibogaine, Memantine, Methoxetamine, Nitrous oxide, Phencyclidine, Rolicyclidine, Tenocyclidine, Methoxydine, Tiletamine, Xenon, Neramexane, Eliprodil, Etoxadrol, Dexoxadrol, WMS-2539, NEFA, Delucemine, 8A-PDHQ, Aptiganel, HU-211, Remacemide, Rhynchophylline, Ketamine, 1-Aminocyclopropanecarboxylic acid (ACPC), 7-Chlorokynurenate' DCKA (5,7-dichlorokynurenic acid), Kynurenic acid, Lacosamide, L-phenylalanine, Neurotransmitters, Psychedelics, Long-term potentiation, and NMDA.

In a further aspect, the TrkB agonist can be selected from the group consisting of a small molecule, protein and an antibody. In some embodiments, the agent that modulates BDNF levels is an ampakine. The ampakine can include an allosteric modulator of the AMPA-receptor.

In some aspects, the pharmaceutical composition further includes a therapeutically effective amount of a GABAR agonist.

BRIEF DESCRIPTION OF THE DRAWINGS

FIGS. 8(A-B) are graphical illustrations of the development of respiratory dysfunction in 8- to 12-week-old Mecp2$^{-/+}$ (Het) mice. A1-A4, Breathing frequency (A1), $T_{tot}$ (A2), $T_i$ (A3), and $T_e$ (A4) are not significantly different between Wt(open bars) and Het (gray bars) mice at 8 weeks of age (Wt, n=7; Het, n=5). Significant increases in frequency, associated with decreased $T_i$, $T_e$, and $T_{tot}$, are observed in 10-week-old Hets compared with Wt controls (Wt, n=22; Het, n=14); these differences persist at 12 weeks (Wt, n=16; Het, n=14) with the exception of $T_i$. Results are expressed as the mean in percentage Wt±SEM. *$p<0.05$, $p<0.01$, *$p<0.001$, unpaired t test. B1, Box-and-whisker plots showing the number of apneas in Wt (open bars) and Het (gray bars) mice at 8, 10, and 12 weeks of age. B2, The proportion of Hets exhibiting significantly more apneas than Wt increased from 20% at 8 weeks to 50% at 12 weeks of age.

FIGS. 9A-D illustrate BDNF protein levels in 8-, 10-, and 12-week-old Mecp2 Het mice. A-C, BDNF levels, measured by ELISA, in the NG (A), medulla (B), and pons (C) of Wt (open bars) and Het mice (gray bars). Results are expressed as the mean in percentage Wt±SEM (n=5-19 NG per group). *$p<0.05$, $p<0.01$, *$p<0.001$, unpaired t test. D, BDNF immunostaining, representative of 3 Wt and 3 Het littermate pairs, demonstrates reduced BDNF levels in the nTS subregion of the dorsomedial medulla in 12-week-old Het animals compared with Wt. AP, area postrema; tS, tractus solitarius.

FIGS. 10A-C are a graphical illustration showing treatment of Mecp2 Het mice with LM22A-4 restores normal respiratory frequency by increasing $T_e$ and $T_{tot}$. Animals were treated from 8 to 12 weeks of age as described in Materials and Methods. A, Representative plethysmographic traces showing the breathing pattern of Wt vehicle-treated, Wt LM22A-4-treated, Het vehicle-treated, and Het LM22A-4-treated mice. B, Comparison of the breathing frequency, $T_{tot}$, $T_i$ and $T_e$ among all four treatment groups. Results are expressed as the mean in percentage Wt±SEM (Wt vehicle-treated, n=29, open bars; Wt LM22A-4 treated, n=13, light gray bars; Het vehicle-treated, n=22, dark gray bars; Het LM22A-4-treated, n_22, black bars). *$p<0.05$, $p<0.01$, *$p<0.001$, ANOVA I with post hoc LSD test. C, Body weight is unaffected by 5 weeks of treatment with LM22A-4 (50 mg/kg, i.p., b.i.d.) Results are shown as mean±SEM (Wt vehicle-treated, n=26, black cross marker; Wt LM22A-4 treated, n=11, dark circle markers; Het vehicle-treated, n=24, open square markers; Het LM22A-4 treated, n_29, dark triangle markers).

DETAILED DESCRIPTION

Figure 1:
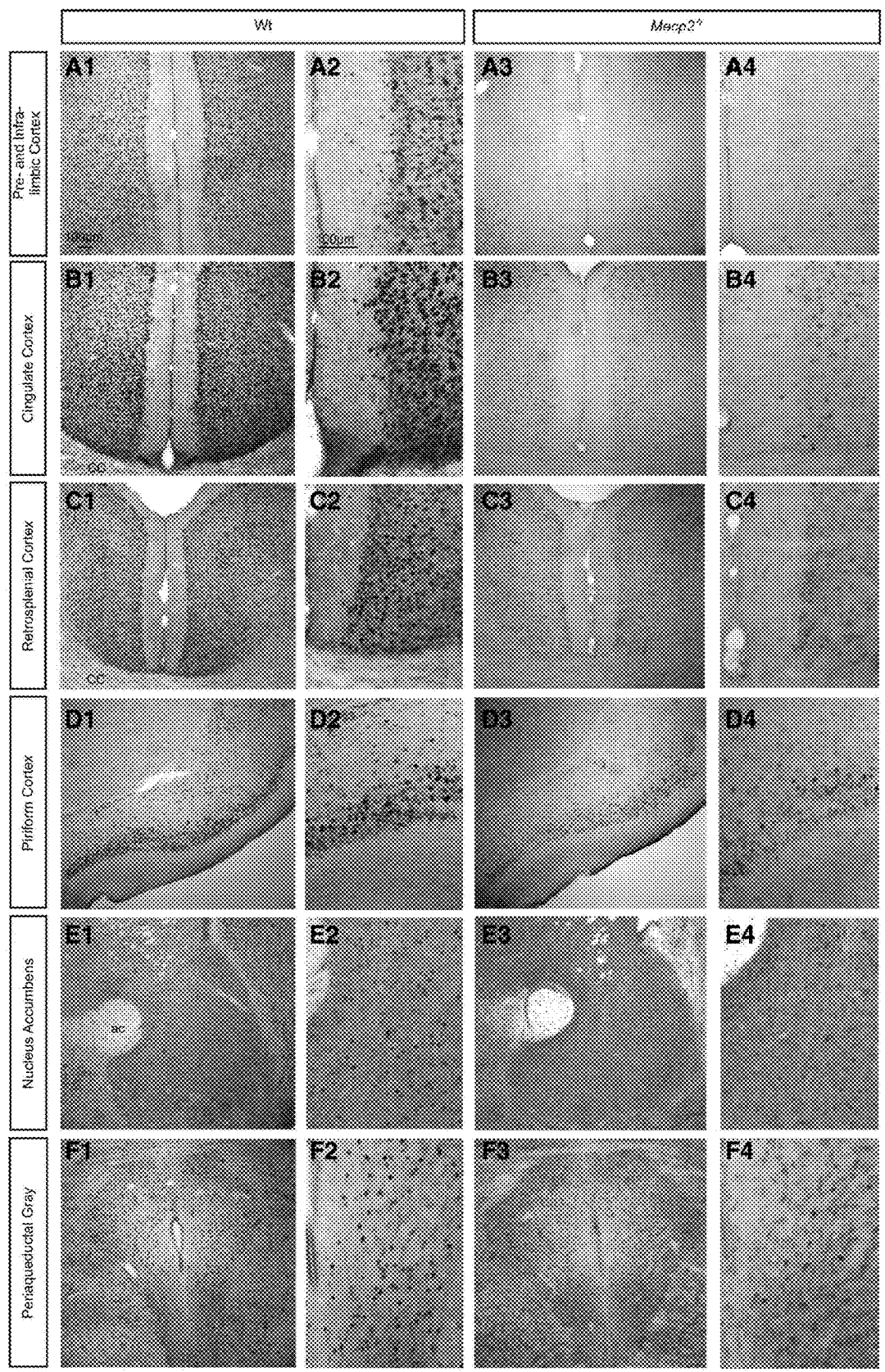
FIGS. 1A-F illustrate photographs showing immunostains of reduced Fos expression in forebrain and midbrain structures in symptomatic Mecp2 Null mice. At 6 weeks of age, Null mice (A3-F4) exhibit markedly reduced levels of Fos expression in a discrete subset of cortical and subcortical structures, including the prelimbic and infralimbic cortices (A), cingulated cortex (B), retrosplenial cortex (C), piriform cortex (D), the nucleus accumbens (E), and periaqueductal gray (F) compared with Wt (A1-F2). A2-F2 and A4-F4 show higher-magnification views of the sections shown in A1-F1 and A3-F3, respectively. ac, Anterior commissure; cc, corpus callosum.

The present invention is not limited to the particular methodology, protocols, and reagents, etc., described herein and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, the term "administering" to a patient includes dispensing, delivering or applying an active compound in a pharmaceutical formulation to a subject by any suitable route for delivery of the active compound to the desired location in the subject (e.g., to thereby contact a brain stem and forebrain neurons), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. Specific routes of administration may include intraperitoneal (i.p.) injection and/or via oral routes.

As used herein an "effective amount" of an agent or combination of agents is an amount sufficient to achieve a desired therapeutic or pharmacological effect, such as an amount that is capable of ameliorating biochemical and functional abnormalities associated with loss-of-function mutations of the gene encoding methyl-CpG binding protein 2 (MeCP2) and/or the amount required to inhibit apneic breathing in a subject having RTT and related disorders. An effective amount of an agent or combinatory therapy as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

As used herein, the tern "therapeutically effective amount" refers to that amount of a composition that results in amelioration of symptoms or a prolongation of survival in a patient. A therapeutically relevant effect relieves to some extent one or more symptoms of a disease or condition or returns to normal either partially or completely one or more physiological or biochemical parameters associated with or causative of the disease or condition, e.g., Rett syndrome.

As used herein, the terms "patient" and "subject" refer to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, ayes, etc.), which is to be the recipient of a particular treatment. Typically, the terms "host," "patient," and "subject" are used interchangeably herein in reference to a human subject.

As used herein, the terms "subject suffering from Rett syndrome", "subject having Rett syndrome" or "subjects identified with Rett syndrome" refers to subjects that are identified or diagnosed as having or likely having a loss-of-function mutation in the gene encoding the methyl-CpG binding protein MeCP2 gene, which causes Rett syndrome.

The term "modulate," as used herein, refers to a change in the biological activity of a biologically active molecule. Modulation can be an increase or a decrease in activity, a change in binding characteristics, or any other change in the; biological, functional, or immunological properties of biologically active molecules.

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

A "known therapeutic compound" refers to a therapeutic compound that has been shown (e.g., through animal trials or prior experience with administration to humans) to be effective in such treatment or prevention.

"Treating" or "treatment" of a condition or disease includes: (1) preventing at least one symptom of the conditions, i.e., causing a clinical symptom to not significantly develop in a mammal that may be predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. Treatment, prevention and ameliorating a condition, as used herein, can include, for example decreasing or eradicating a deleterious or harmful condition associated with Rett syndrome. Examples of such treatment include: decreasing breathing abnormalities, decreasing motor dysfunction, and improving respiratory and neurological function.

"Cyano" refers to the group —CN.

"Halogen" or "halo" refers to fluorine, bromine, chlorine, and iodine atoms.

"Hydroxy" refers to the group —OH.

"Thiol" or "mercapto" refers to the group —SH.

"Sulfamoyl" refers to the —$SO_2NH_2$.

"Alkyl" refers to a cyclic, branched or straight chain, alkyl group of one to eight carbon atoms. The term "alkyl" includes reference to both substituted and unsubstituted alkyl groups. This term is further exemplified by such groups as methyl, ethyl, n-propyl, i-propyl, n-butyl, t-butyl, i-butyl (or 2-methylpropyl), cyclopropylmethyl, cyclohexyl, i-amyl, n-amyl, and hexyl. Substituted alkyl refers to alkyl as just described including one or more functional groups such as aryl, acyl, halogen, hydroxyl, amido, amino, acylamino, acyloxy, alkoxy, cyano, nitro, thioalkyl, mercapto and the like. These groups may be attached to any carbon atom of the lower alkyl moiety. "Lower alkyl" refers to $C_1$-$C_6$ alkyl, with $C_1$-$C_4$ alkyl more preferred. "Cyclic alkyl" includes both mono-cyclic alkyls, such as cyclohexyl, and bi-cyclic alkyls, such as bicyclooctane and bicycloheptane. "Fluoroalkyl" refers to alkyl as just described, wherein some or all of the hydrogens have been replaced with fluorine (e.g., —$CF_3$ or —$CF_2CF_3$).

"Aryl" or "Ar" refers to an aromatic substituent which may be a single ring or multiple rings which are fused together, linked covalently, or linked to a common group such as an ethylene or methylene moiety. The aromatic ring(s) may contain a heteroatom, such as phenyl, naphthyl, biphenyl, diphenylmethyl, 2,2-diphenyl-1-ethyl, thienyl, pyridyl and quinoxalyl. The term "aryl" or "Ar" includes reference to both substituted and unsubstituted aryl groups. If substituted, the aryl group may be substituted with halogen atoms, or other groups such as hydroxy, cyano, nitro, carboxyl, alkoxy, phenoxy, fluoroalkyl and the like. Additionally, the aryl group may be attached to other moieties at any position on the aryl radical which would otherwise be occupied by a hydrogen atom (such as 2-pyridyl, 3-pyridyl and 4-pyridyl).

The term "alkoxy" denotes the group —OR, where R is lower alkyl, substituted lower alkyl, aryl, substituted aryl, aralkyl or substituted aralkyl as defined below.

The term "acyl" denotes groups —C(O)R, where R is alkyl, substituted alkyl, alkoxy, aryl, substituted aryl, amino and alkylthiol.

"Carbocyclic moiety" denotes a ring structure in which all ring vertices are carbon atoms. The term encompasses both single ring structures and fused ring structures. Examples of aromatic carbocyclic moieties are phenyl and naphthyl.

"Heterocyclic moiety" denotes a ring structure in which one or more ring vertices are atoms other than carbon atoms, the remainder being carbon atoms. Examples of non-carbon atoms are N, O, and S. The term encompasses both single ring structures and fused ring structures. Examples of aromatic heterocyclic moieties are pyridyl, pyrazinyl, pyrimidinyl, quinazolyl, isoquinazolyl, benzofuryl, isobenzofuryl, benzothiofuryl, indolyl, and indolizinyl.

The term "amino" denotes the group NRR', where R and R' may independently be hydrogen, lower alkyl, substituted lower alkyl, aryl, substituted aryl as defined below or acyl.

The term "amido" denotes the group —C(O)NRR', where R and R' may independently be hydrogen, lower alkyl, substituted lower alkyl, aryl, substituted aryl as defined below or acyl.

The term "independently selected" is used herein to indicate that the two R groups, $R^1$ and $R^2$, may be identical or different (e.g., both $R^1$ and $R^2$ may be halogen or, $R^1$ may be halogen and $R^2$ may be hydrogen, etc.).

Embodiments described herein relate to compositions and methods of treating pervasive development disorders, such as Rett Syndrome or autism spectrum disorder, in a subject. It was found that loss of function mutations in Mecp2, the gene mutated in Rett syndrome (RTT), disrupts the balance of excitation and inhibition between the forebrain and brainstem in mouse models of the disease. Without being bound by theory, it is believed that perturbations of circuit function within and between the forebrain and brainstem are at least partially responsible for the pathophysiology of pervasive development disorders, such as RTT, i.e., the combination of deficits (hypoactivity) in forebrain-mediated functions, such as cognition, social communication and motor control on the one hand, and dysregulation (hyperexcitability) of brainstem-mediated functions, such as breathing, on the other.

Using Fos protein as a surrogate marker of neuronal activity, it was found that RTT mice exhibit reduced activity throughout the forebrain, including reduced activity in structures critical for sensorimotor processing, cognition, motor control and social communication. It was also found that treatment of RTT mice with a low, subanesthetic dose of an N-methyl-D-aspartate receptor (NMDAR) antagonist acutely reverses hypoactivity in forebrain circuits and significantly improves at least one measure of forebrain function, i.e., prepulse inhibition of acoustic startle without altering brainstem hyperactivity.

In some embodiments, an NMDAR antagonist can be administered to a subject having or suspected of having a pervasive development disorder, such as RTT or autism spectrum disorder, to prevent, ameliorate or reverse hypoactivity in forebrain circuits and/or substantially improve at least one measure of forebrain function, i.e., prepulse inhibition of acoustic startle. Accordingly, a method for treating a pervasive development disorder, such as RTT, can include administering an NMDAR antagonist to a subject such that when administered the NMDAR antagonist alleviates the core neurological symptoms of a pervasive development disorder, such as RTT, by re-establishing the normal balance between excitation and inhibition within and between the forebrain and brainstem, respectively.

Figure 14:
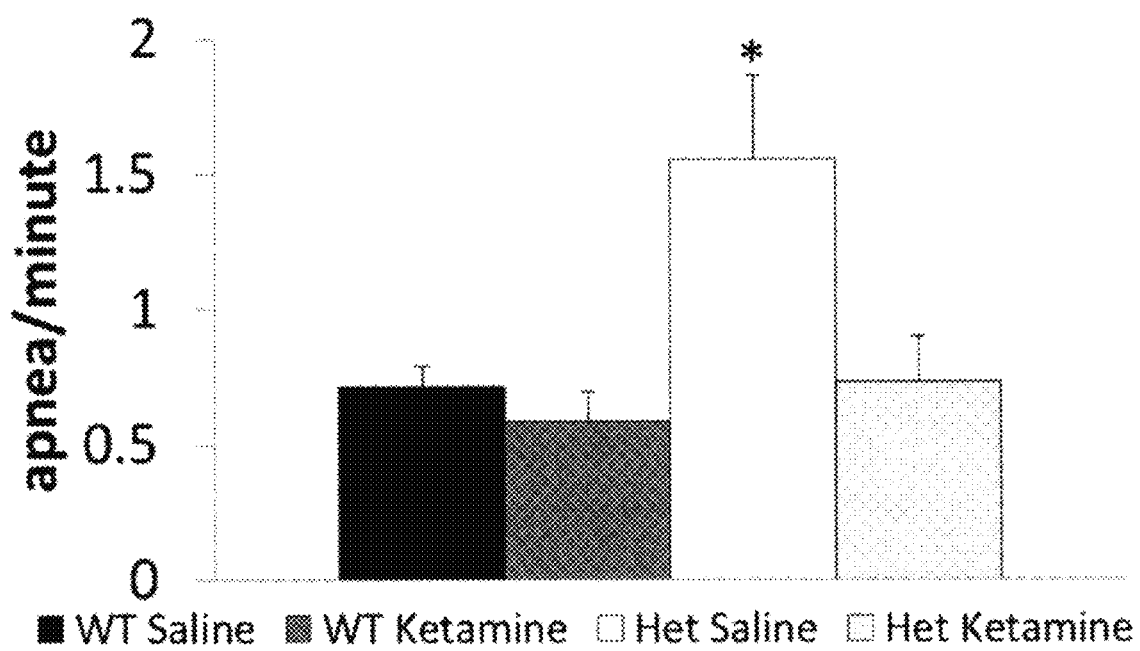
FIG. 14 illustrates a very low dose ketamine (3 mg/kg) dosing regimen for the treatment of RTT in miceMecp2Jae OC females treated once every 72 hours for two weeks (saline or Ketamine 3 mg/kg) with plethysmography measurement 24 hours after the last injection.

It has been observed that repeated intermittent dosing with the NMDAR antagonist, ketamine, at subanesthetic doses results in complete elimination of apneic breathing, a core feature of RTT and related disorders, in a disease model (FIG. 14). Other embodiments described herein therefore relate to an intermittent dosing regimen for the treatment of a pervasive development disorder in a subject. The intermittent dosing regimen can include administering a subanesthetic dose of an NMDAR antagonist to the subject at a dosing interval for a period of time, then withholding administration of the NMDAR antagonist for a period of time, and then, if necessary, again administering the NMDAR antagonist at a dosing interval for a period of time. This dosing regimen can be repeated until at least one symptom of the pervasive development disorder is alleviated or the underlying substrate or pathology of the disorder is altered such that relief or alleviation of the symptom is sustained. A therapeutically effective amount may be achieved by multiple dosing. The intermittent regimen may be repeated depending on the response in the subject that is being sought.

In some embodiments, the subanesthetic dose of the NMDAR antagonist is administered at a dosing interval effective to alleviate at least one symptom associated with the pervasive development disorder. The dosing interval of the NMDAR antagonist is then stopped or withheld once the at least one symptom has been at least partially or substantially alleviated. The dosing interval of the subanesthetic dose of the NMDAR antagonist can then be resumed upon recurrence of the at least one symptom. For example, the subanesthetic dose of the NMDAR antagonist can be initially administered to the subject over a multi-day dosing interval. Administration of the subanesthetic dose of the NMDAR antagonist can be stopped once the at least one symptom is at least partially or substantially alleviated. The dosing interval of the NMDAR antagonist can then be resumed to the subject upon recurrence of the at least one symptom for time period effective to alleviate the at least one symptom. The dosing regimen can be repeated as necessary to alleviate the at least one symptom.

Subanesthetic dose levels of an NMDAR antagonist, such as ketamine, for example, administered via injection, such as intravenous or subcutaneous injection, range from about 0.1 mg/kg to about 10 mg/kg bodyweight. For example, the dose levels of ketamine can range from about 0.1 mg/kg to about 5 mg/kg, from about 0.7 mg/kg to about 5 mg/kg, from about 1 mg/kg to about 2 mg/kg, from about 2 mg/kg to about 6 mg/kg, from about 1 mg/kg to about 3 mg/kg, about 2 mg/kg to about 3 mg/kg, from about 3 mg/kg to about 5 mg/kg, from about 5 mg/kg to about 7 mg/kg, from about 0.3 mg/kg to about 4 mg/kg, from about 0.3 mg/kg to about 3.5 mg/kg, from about 1.0 mg/kg to about 1.5 mg/kg, or from about 1 mg/kg to less than about 10 mg/kg.

In some embodiments, the NMDAR antagonist can be administered to the subject at dosing intervals of at least 12 hours. For example, the dosing interval can be at least 12 hours, 24 hours, 36 hours, 48 hours, 72 hours, 96 hours, 1 day, 2 days, 3 days, 4 days, 5 days, 6 days, 7 days, 8 days, 9 days, 10 days, 11 days, 12 days, 13 days, 14 days, 90 days, 1 week, 2 weeks, 3 weeks, 4 weeks, or longer, or any combination or increment thereof.

In some embodiments, the at least one symptom of the pervasive development disorder alleviated by administration of the NMDAR antagonist can include a motor, respiratory and/or autonomic dysfunction and/or seizures associated with the pervasive development disorder (e.g., Rett syndrome). For example, the at least one symptom can include loss of normal movement and coordination, loss of communication ability, abnormal hand movements, such as hand wringing, squeezing, clapping, tapping, or rubbing, unusual eye movements, such as intense staring, blinking, crossed eyes or closing one eye at a time, breathing or respiratory problems, such as hyperventilation and apneic breathing, agitation and irritability, cognitive disabilities, seizures, irregular heartbeat, pain, as well as problems with chewing and swallowing and teeth grinding.

The periods of time for dosing, withholding dosing, and re-administering dosing may be of the same or of different length. The length of each period can be expressed in days or in weeks and, dependent upon the specific NMDAR antagonist that is being used and the response of the subject, may range from 1 to 60 days or from 1 to 8 weeks. The total length of time of a dosing regimen can range from about 1 week to about 8 weeks. In certain embodiments, the total length of time of a dosing regimen lasts for about 2 weeks.

The intermittent regimen may be repeated two, three, four or more times depending on the response in the subject that is being sought. The period of time between two intermittent dosing regimens is variable and can range from 1 to 12 months, as needed.

In some embodiments, the NMDAR antagonist can include an agent capable of antagonizing, or inhibiting the action of, the N-Methyl-D-aspartate receptor. Examples of NMDAR antagonists include, but are not limited to: NMDA site antagonists, such as DL-AP7 (DL-2-Amino-7-phosphonoheptanoic acid), DL-AP5 (DL-2-Amino-5-phosphonopentanoic acid), D-AP5 (D-(−)-2-Amino-5-phosphonopentanoic acid), L-AP5 (L-(+)-2-Amino-5-phosphonopentanoic acid), D-AP7 (D-(−)-2-Amino-7-phosphonoheptanoic acid), (RS)—CPP ((RS)-3-(2-Carboxypiperazin-4-yl)-propyl-1-phosphonic acid), (R)—CPP (3-((R)-2-Carboxypiperazin-4-yl)-propyl-1-phosphonic acid), (R)-4CPG ((R)-4-Carboxyphenylglycine), LY 235959 ([3S-3a,4aa,6b,8aa)]-Decahydro-6-(phosphonomethyl)3isoquinolinecarboxylic acid)), ((CGS-19755)); Competitive NMDA antagonists such as: selfotel CGS 19755 (cis-4-[Phoshomethyl]-piperidine-2-carboxylic acid), SDZ 220-581 ((S)-α-Amino-2'-chloro-5-(phosphonomethyl)[1,1'-biphenyl]-3-propanoic acid), SDZ 220-040 ((S)-α-Amino-2',4'-dichloro-4-hydroxy-5-(phosphonomethyl)-[1,1'-biphenyl]-3-propanoic acid), CGP 37849 ((E)-(±)-2-Amino-4-methyl-5-phosphono-3-pentenoic acid), CGP 39551 ((E)-(±)-2-Amino-4-methyl-5-phosphono-3-pentenoic acid ethyl ester); Glycine Site Antagonists such as D-cycloserine, CNQX (6-Cyano-7-nitroquinoxalme-2,3 dione), 7-Chlorokynurenic acid (7-Chloro-4-hydroxyquinoline-2-carboxylic acid), ACBC (1-Aminocyclobutane-1-carboxylic acid), 7-Chlorokynurenate, (S)-(−)-HA-966 ((S)-(−)-3-Ammo-1-hydroxypyrrolidin-2-one), 5,7-Dichlorokynurenic acid (DCKA, 5,7-Dichloro-4-hydroxyquinoline-2-carboxylic acid), L-701,252 (7-Chloro-3-(cyclopropylcarbonyl)-4-hydroxy-2(1H)-quinolinone), L-689,560 (trans-2 Carboxy-5,7-dichloro-4-phenylaminocarbonylamino-1,2,3,4-tetrahydroquinoline), Felbamate (2-Phenyl-1,3-propanedioldicarbamate), L-701,324 (7-Chloro-4-hydroxy-3-(3-phenoxy)phenyl-2(1H)-quinolinone), CGP 78608 hydrochloride ([(1S)-1-[[(7-Bromo-1,2,3,4-tetrahydro-2,3-dioxo-5-quinoxalinyl)methyl]amino]ethyl]phosphonic acid hydrochloride), Gavestinel (GV-150,526), Lacosamide, L-phenylalanine, 1-Aminocyclopropanecarboxylic acid (ACPC); Ion Channel Antagonists such as (±)-1-(1,2-Diphenylethyl)piperidine maleate, Dizocilpine ((+)-MK 801 maleate), (5S, 10R)-(+)-5-Methyl-10,11-dihydro-5H-dibenzo[a,d]cyclohepten-5,10-imine maleate, (−)-MK 801 maleate ((5R,10S)-(−)-5-Methyl-10,11-dihydro-5H-dibenzo[a,d]cylcohepten-5,10-imine maleate), Loperamide hydrochloride (4-(4-Chlorophenyl)-4-hydroxy-N,N-dimethyl-a,a-diphenyl-1-piperidinebutanamide hydrochloride), Remacemide hydrochloride (2-Amino-N-(1-methyl-1,2-diphenylethyl)acetamide hydrochloride), IEM 1460 (N,N,N,-Trimethyl-5-[(tricyclo[3.3.1.13,7]dec-1-ylmethyl)amino]-1-pentanaminiumbromide hydrobromide), ketamine, Norketamine hydrochloride (2-Amino-2-(2-chlorophenyl)cyclohexanone hydrochloride), N20C hydrochloride (2-[(3,3-Diphenylpropyl)amino]acetamide hydrochloride), dextromethorphan, AZD6765 (Lanicemine), Aptiganel (Cerestat, CNS-1102), HU-211, Rhynchophylline, Amantadine and related compounds, nitromemantine, Memantine (hydrochloride 3,5-Dimethyl-tricyclo[3.3.1.13.7]decan-1-amine hydrochloride) and rimantidine and similar derivatives described in U.S. Pat. Nos. 6,071,876, 5,801,203, 5,747,545, 5,614,560, 5,506,231, PCT Applications 01/62706 and WO 01/48516, Dextrallorphan, Dextromethorphan (DXM) and analogs thereof described in U.S. Pat Pub No: 20100137448, Dextrorphan, Diphenidine, Ethanol, Eticyclidine, Gacyclidine, Ibogaine, Magnesium, Methoxetamine, Nitrous oxide, Phencyclidine (PCP), Rolicyclidine, Tenocyclidine, Methoxydine(4-meo-pcp), Tiletamine, Xenon, Neramexane (1,3,3,5,5-pentamethylcyclohexanamine), Etoxadrol, Dexoxadrol, WMS-2539, NEFA, Delucemine, 8A-PDHQ; polyamine site antagonists such as spermine, N-(4-Hydroxyphenylacetyl)spermine N—(N-(4-Hydroxyphenylacetyl)-3-ammopropyl)-(N'-3-aminopropyl)-1,4-butanediamine, N-(4-Hydroxyphenylpropanoyl)spermine trihydrochloride (N—(N-(4Hydroxyphenylpropanoyl)-3-aminopropyl)-(N'-3-ammopropyl)-1,4-butanediamine trihydrochloride), Arcaine sulfate (N,N'-1,4-Butanediylbisguanidine sulfate), Ifenprodil hemitartrate (2-(4-Benzylpiperidino)-1-(4-hydroxyphenyl)-1-propanol hemitartrate), Synthalin sulfate (N,N'-1, 10-Decanediylbisguanidine sulfate), Eliprodil (a-(4-Chlorophenyl)-4-[(4-fluorophenyl)methyl]-1-piperidineethanol); other NMDA selective Antagonists such as the NR2B antagonists Ro 25-6981 maleate ((αR,βS)-α-(4-Hydroxyphenyl)-β-methyl-4-(phenylniethyl)-1-piperidinepropanol maleate) (CP101,606 or Traxoprodil), Bilobalide, Lipocortin-1, Cerebral Fluid Zinc level elevators, riluzole, ifenprodil, iamotrigine, spermidines, flupirtine, levernopamil, 1-phenyl-2-(2-pyridyl)ethanamine), agniatine; synthetic opioids such as Meperidine, Methadone, Dextropropoxyphene, Tramadol and Ketobemidone; compounds having NMDA-antagonist-like properties including hydrogenated pyrido[4,3-b]indole, dimebon described in U.S. Pat Pub. No. U.S. 2010/0178277 and Huperzine A.

In some embodiments, the NMDAR antagonist is selected from Amantadine, AZD6765, Dextrallorphan, Dextromethorphan, Dextrorphan, Diphenidine, Dizocilpine (MK-801), Ethanol, Eticyclidine, Gacyclidine, Ibogaine, Memantine, Methoxetamine, Nitrous oxide, Phencyclidine, Rolicyclidine, Tenocyclidine, Methoxydine, Tiletamine, Xenon, Neramexane, Eliprodil, Etoxadrol, Dexoxadrol, WMS-2539, NEFA, Remacemide, Delucemine, 8A-PDHQ, Aptiganel, HU-211, Remacemide, Rhynchophylline, Ketamine, 1-Aminocyclopropanecarboxylic acid (ACPC), 7-Chlorokynurenate' DCKA (5,7-dichlorokynurenic acid), Kynurenic acid, Lacosamide, L-phenylalanine, Neurotransmitters, Psychedelics, Long-term potentiation, and NMDA. In particular embodiments, the NMDAR antagonist is selected from ketamine, remacemide, and D-cycloserine.

In other embodiments, the NMDAR antagonist can be a low-trapping NMDAR channel blocker. An example of a low-trapping NMDAR channel blocker is an arylalkylamine having the following formula:

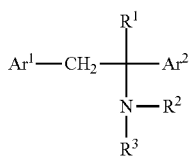

wherein, $Ar^1$ and $Ar^2$, which may be the same or different, independently represent phenyl or phenyl substituted by one or more of amino, nitro, halogen, hydroxy, $C_1$-$C_6$ alkoxy, $C_1$-$C_6$ alkyl or cyano;
$R^1$ represents hydrogen, $C_1$-$C_6$ alkyl, $C_1$-$C_6$ alkoxycarbonyl;
$R^2$ represents hydrogen or $COCH_2\ NH_2$;
$R^3$ represents hydrogen or $C_1$-$C_6$ alkyl;
in addition, when $R^2$ represents hydrogen either one or both of $Ar^1$ and $Ar^2$ may also represent 2-, 3- or 4-pyridinyl and $R^1$ may also represent trihalomethyl;
or a pharmaceutically acceptable salt thereof.

Examples of NMDAR antagonists having the above noted formula include:
1,2-diphenylethylamine;
1,2-diphenyl-2-propylamine;
1,2-bis(4-fluorophenyl)-2-propylamine;
1,2-diphenyl-2-butylamine;
(−)1,2-diphenyl-2-propylamine;
(+)1,2-diphenyl-2-propylamine;
2,3-diphenyl-2-aminopropanoic acid methyl ester;
N-methyl-1,2-diphenyl-2-propylamine;
N-methyl-1,2-diphenylethylamine;
1-(3-nitrophenyl)-2-phenyl-2-propylamine;
1-(3-chlorophenyl)-2-phenyl-2-propylamine;
1-(3-bromophenyl)-2-phenyl-2-propylamine;
1-(3-cyanophenyl)-2-phenyl-2-propylamine;
2-(2-methylphenyl)-1-phenyl-2-propylamine;
1-(4-chlorophenyl)-2-phenyl-2-propylamine;
1-phenyl-2-(3,4-dichlorophenyl)-2-propylamine;
1-phenyl-2-(3-methoxyphenyl)-2-propylamine;
1-(4-hydroxyphenyl)-2-phenyl-2-propylamine;
1-(4-hydroxyphenyl)-2-phenylethylamine;
1-phenyl-2-(4-hydroxyphenyl)ethylamine;
1,2-bis(4-hydroxyphenyl)ethylamine;
1-phenyl-2-(4-hydroxyphenyl)-2-propylamine;
1,2-bis(4-hydroxyphenyl)-2-propylamine;
1-(2-pyridinyl)-2-phenylethylamine;
1-(3-pyridinyl)-2-phenylethylamine;
1-(4-pyridinyl)-2-phenylethylamine;
1-phenyl-2-(2-pyridinyl)ethylamine;
1-phenyl-2-(3-pyridinyl)ethylamine;
1-phenyl-2-(4-pyridinyl)ethylamine;
N-methyl-1-(3-pyridinyl)-2-phenylethylamine;
3,3,3-trifluoro-1,2-diphenyl-2-propylamine;
N-methyl-3,3,3-trifluoro-1,2-diphenyl-2-propylamine;
2-amino-N-(1,2-diphenyl-1-methylethyl)acetamide;
2-amino-N-(1,2-diphenylethyl)acetamide; and
2-amino-N-[1,2-bis(4-fluorophenyl)-1-methylethyl]acetamide.

The compounds described above are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids. Methods of making the compounds described above are disclosed, for example, in U.S. Pat. No. 5,605,916, which is incorporated herein by reference in its entirety.

In other embodiments, the NMDAR antagonist can be a low-trapping NMDAR channel blocker having the following formula:

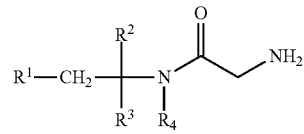

where:
$R^1$ and $R^2$ are independently phenyl or 4-fluorophenyl;
$R^3$ is hydrogen, C1-6 alkyl or methoxycarbonyl;
$R^4$ is hydrogen or methyl; and pharmaceutically acceptable salts thereof or an active metabolite thereof.

In still other embodiments, the low-trapping NMDAR channel blocker can include 2-amino-N-(1,2-diphenyl-1-methylethyl)acetamide (remacemide) or a pharmaceutically acceptable salt thereof (e.g., hydrochloride salt) or its active metabolite. Examples of active metabolites of remacemide include desglycinyl metabolites, such as FPL 12495 or ARL 12495AA, FPL 14331, FP1 14465, FPL 15455, FPL 14991, FPL 14981, FPL 13592, and FPL 15112. In some embodiments, the active metabolite can be FPL 12495 or ARL 12495AA.

In some embodiments, the NMDAR antagonist can be administered in combination with a TrkB agonist and/or an agent that modulates BDNF levels (e.g., in a combination therapy) to treat a pervasive development disorder, such as RTT or autism spectrum disorder. It was found that RTT mice exhibit increased activity, associated with synaptic hyperexcitability (measured electrophysiologically) in brainstem circuits critical for respiratory and autonomic control. Hyperexcitability in brainstem respiratory and autonomic circuits is associated with deficits in Brain Derived Neurotrophic Factor (BDNF) and reduced activation of its receptor, TrkB. Moreover, exogenous BDNF and the small molecule TrkB ligand, LM22A-4 acutely reverse synaptic hyperexcitability in these circuits and eliminate apneic breathing in vivo.

The phrase "combination therapy" embraces the administration of a NMDAR antagonists and a TrkB agonist as well as an agent that modulates BDNF levels as part of a specific treatment regimen intended to provide a beneficial effect from the co-action of these therapeutic agents. When administered as a combination, the NMDAR antagonist and the TrkB agonist and/or an agent that modulates BDNF levels can be formulated as separate compositions or in a single composition. Administration of these therapeutic agents in combination typically is carried out over a defined time period (usually minutes, hours, days or weeks depending upon the combination selected). When administered as a combination and the NMDAR antagonist and the TrkB agonist are formulated as separate compositions, the TrkB agonist can be administered in accordance with an NMDAR antagonist intermittent dosing regimen described above or as a separate dosing regimen as needed.

When formulated as separate compositions, "combination therapy" is intended to embrace administration of these therapeutic agents in a sequential manner, that is, wherein each therapeutic agent is administered at a different time, as well as administration of these therapeutic agents, in a substantially simultaneous manner. Sequential or substantially simultaneous administration of each therapeutic agent can be effected by any appropriate route including, but not limited to, intraperitoneal routes, oral routes, intravenous routes, intramuscular routes, and direct absorption through mucous membrane tissues. The therapeutic agents can be administered by the same route or by different routes. For example, a first therapeutic agent of the combination selected may be administered by intraperitoneal injection while the other therapeutic agents of the combination may be administered orally. Alternatively, for example, all therapeutic agents may be administered by intraperitoneal injection or all therapeutic agents may be administered orally. The sequence in which the therapeutic agents are administered is not narrowly critical. "Combination therapy" also can embrace the administration of the therapeutic agents as described herein in further combination with other biologically active ingredients, known therapeutic compounds and/or non-drug therapies (e.g., surgery).

A TrkB agonist for use in a combination therapy with the NMDAR antagonist can include any agent capable of directly activating or indirectly promoting the activation of TrkB. For example, a TrkB agonist capable of directly activating TrkB can include TrkB activating antibodies (described in Qian et al., *Novel agonist monoclonal antibodies activate TrkB receptors and demonstrate potent neurotrophic activities*. J Neurosci 2006; 26:9394-9403 and US2010/0297115). A TrkB agonist capable of directly activating TrkB can also include small molecules that function as direct and specific TrkB activating ligands, such as but not limited to 7,8-dihydroxyflavone (7,8-DHF) (described in Jang et al., *A selective TrkB agonist with potent neurotrophic activities by 7,8-dihydroxyflavone*. Proc Natl Acad Sci USA 2010; 107:268) and the non-peptide BDNF loop 2 domain mimetic, LM22A-4 (described in Massa et al., *Small molecule BDNF mimetics activate TrkB signaling and prevent neuronal degeneration in rodents*. J Clin Invest. 2010; 120(5):1774-1785).

In some aspects, the TrkB agonist is an agent that transactivates TrkB including but not limited to adenosine or an adenosine agonist such as CGS 21680 described in Lee and Chao, *Activation of Trk neurotrophin receptors in the absence of neurotrophins*, Proc Natl Acad Sci USA. 2001 Mar. 13; 98(6):3555-60).

Mature brain-derived neurotrophic factor (BDNF) is a secreted protein that, in humans, is encoded by the BDNF gene. BDNF acts via two receptors, the p75 neurotrophin receptor and the TrkB tyrosine kinase receptor. In some embodiments, an agent that modulates BDNF levels can include any agent capable of modulating (e.g., increasing) BDNF levels and/or BNDF activation of TrkB in a subject. For example, such agents can include BDNF itself and known therapeutic compounds that promote endogenous BDNF production in a subject including but not limited to ampakines, inhibitors of BDNF gene repression, mixed lineage kinase inhibitors, and antidepressants.

Examples of ampakines can be allosteric modulators of the AMPA-receptor. "α-amino-3-hydroxy-5-methyl-isoxazole-4-propionic acid", or "AMPA", or "glutamatergic" receptors are molecules or complexes of molecules present in cells, particularly neurons, usually at their surface membrane, that recognize and bind to glutamate or AMPA. The binding of AMPA or glutamate to an AMPA receptor normally gives rise to a series of molecular events or reactions that result in a biological response. The biological response may be the activation or potentiation of a nervous impulse, changes in cellular secretion or metabolism, or causing cells to undergo differentiation or movement. Allosteric modulators of the AMPA-receptor that can be used for practicing the methods described herein and methods of making these compounds are disclosed in U.S. Pat. Nos. 5,488,049; 5,650,409; 5,736,543; 5,747,492; 5,773,434; 5,891,876; 6,030,968; 6,274,600 B1; 6,329,368 B1; 6,943,159 B1; 7,026,475 B2 and U.S. Application 20020055508. The disclosures of these publications are incorporated herein by reference in their entireties, especially with respect to the ampakines disclosed therein.

In some embodiments, the ampakine compound can include those compounds having the following general Formula I:

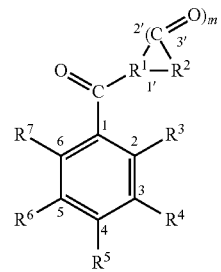

In this formula:
$R^1$ is a member selected from the group consisting of N and CH;
m is 0 or 1;
$R^2$ is a member selected from the group consisting of $(CR^8_2)_{n-m}$ and $C_{n-m}R^8_{2(n-m)-2}$, in which n is 4, 5, 6, or 7, the $R^8$'s in any single compound being the same or different, each $R^8$ being a member selected from the group consisting of H and $C_1$-$C_6$ alkyl, or one $R^8$ being combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2CH_2$, CH=CH, O, NH, N($C_1$-$C_6$ alkyl), N=CH, N=C($C_1$-$C_6$ alkyl), C(O), O—C(O), C(O)—O, CH(OH), NH—C(O), and N($C_1$-$C_6$ alkyl)-C(O);
$R^3$, when not combined with any $R^8$, is a member selected from the group consisting of H, $C_1$-$C_6$ alkyl, and $C_1$-$C_6$ alkoxy;
$R^4$ is either combined with $R^5$ or is a member selected from the group consisting of H, OH, and $C_1$-$C_6$ alkoxy;
$R^5$ is either combined with $R^4$ or is a member selected from the group consisting of H, OH, $C_1$-$C_6$ alkoxy, amino, mono($C_1$-$C_6$ alkyl)amino, di($C_1$-$C_6$ alkyl)amino, and $CH_2OR^9$, in which $R^9$ is a member selected from the group consisting of H, $C_1$-$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$-$C_3$ alkyl, $C_1$-$C_3$ alkoxy, hydroxy, halo, amino, alkylamino, dialkylamino, and methylenedioxy;

$R^6$ is either H or $CH_2OR^9$;

$R^4$ and $R^5$ when combined form a member selected from the group consisting of:

in which: $R^{10}$ is a member selected from the group consisting of O, NH and $N(C_1$-

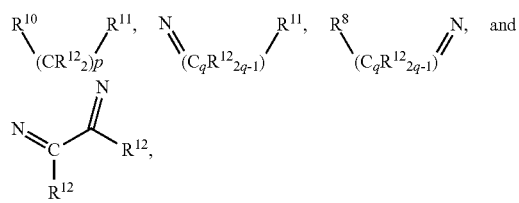

$C_6$ alkyl);

$R^{11}$ is a member selected from the group consisting of O, NH and $N(C_1$-$C_6$ alkyl);

$R^{12}$ is a member selected from the group consisting of H and $C_1$-$C_6$ alkyl, and when two or more $R^{12}$'s are present in a single compound, such $R^{12}$'s are the same or different;

p is 1, 2, or 3; and q is 1 or 2; and $R^7$, when not combined with any $R^8$, is a member selected from the group consisting of H, $C_1$-$C_6$ alkyl, and $C_1$-$C_6$ alkoxy.

A further class of ampakine compounds is those of Formula II:

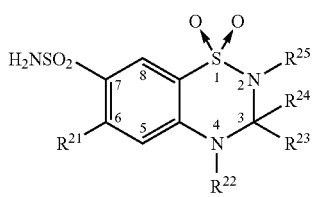

In Formula II:

$R^{21}$ is either H, halo or $CF_3$;

$R^{22}$ and $R^{23}$ either are both H or are combined to form a double bond bridging the 3 and 4 ring vertices;

$R^{24}$ is either H, $C_1$-$C_6$ alkyl, $C_5$-$C_7$ cycloalkyl, $C_5$-$C_7$ cycloalkenyl, Ph, $CH_2$ Ph, $CH_2$ $SCH_2$ Ph, $CH_2$ X, $CHX_2$, $CH_2$ $SCH_2$ $CF_3$, $CH_2$ $SCH_2$ CH=$CH_2$, or

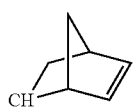

and $R^{25}$ is a member selected from the group consisting of H and $C_1$-$C_6$ alkyl.

A particularly preferred compound is 1-(Quinoxalin-6-ylcarbonyl)piperidine, having the following structure:

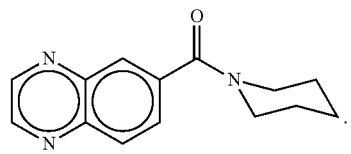

Another particularly preferred compound is 1-(1,4-benzodioxan-6-ylcarbonyl)piperidine, having the following structure:

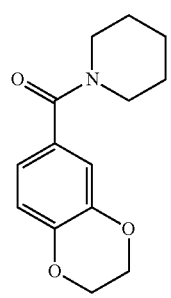 [SMILES: O=C(c1ccc2c(c1)OCCO2)N1CCCCC1]

In another embodiment, the ampakine is a compound of formula III:

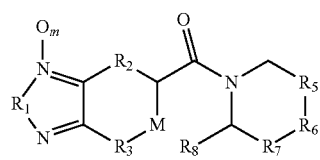

in which:

$R^1$ is oxygen or sulfur;

$R^2$ and $R^3$ are independently selected from the group consisting of —N=, —CR=, and —CX=;

M is =N or =$CR^4$—, wherein $R^4$ and $R^8$ are independently R or together form a single linking moiety linking M to the ring vertex 2', the linking moiety being selected from the group consisting of a single bond, —$CR_2$—, —CR=CR—, —C(O)—, —O—, —S(O)$_y$—, —NR—, and —N=;

$R^5$ and $R^7$ are independently selected from the group consisting of —($C_2$)$_n$—, —C(O)—, —CR=CR—, —CR=CX—, —C(RX)—, —$CX_2$—, —S—, and —O—; and $R^6$ is selected from the group consisting of —($CR_2$)$_m$—, —C(O)—, —CR=CR—, —C(RX)—, —$CR_2$—, —S—, and —O—;

Wherein

X is —Br, —Cl, —F, —CN, —$NO_2$, —OR, —SR, —$NR_2$, —C(O)R—, —$CO_2$ R, or —$CONR_2$; and R is hydrogen, $C_1$-$C_6$ branched or unbranched alkyl, which may be unsubstituted or substituted with one or more functionalities defined above as X, or aryl, which may be unsubstituted or substituted with one or more functionalities defined above as X;

m and p are independently 0 or 1;

n and y are independently 0, 1 or 2.

The ampakine compounds described above for use in the methods described herein can be prepared by conventional methods known to those skilled in the art of synthetic organic chemistry as described in US Pat Pub No: 20100035877A1.

Additional agents capable of increasing BDNF or BDNF activation of TrkB in a subject include AMPA selective compounds that enhance the stimulation of AMPA receptors and/or BDNF expression in the brain stem. Exemplary AMPA selective compounds for use herein include but are not limited to benzoxazines, such as the pyrolidine derivative racetam drugs piracetam and aniracetam, the CX- series of drugs which encompass a range of benzoylpiperidine and benzoylpyrrolidine structures, such as CX-546, CX-614, CX-691, CX-717, Org 26576, CX-701, CX-1739, CX-1763 and CX-1837, benzothiazide derivatives such as cyclothiazide and IDRA-21, biarylpropylsulfonamides such as LY-392,098, LY-404,187, LY-451,646 and LY-503,430, 4-(benzofuran-5-yl carbonyl)morpholine, substituted benzotriazinone and substituted benzopyrimidione described in US2010/02067728, bicyclic amides described in U.S. Pat. No. 8,119,632, and 3-substituted benzo-1,2,3]-triazin-4-one compounds described in US2010/0041647. Other agents capable of increasing BDNF in the subject can include Fingolimod and Copaxone.

In addition to BDNF and the transporter and receptor NMDA, loss of function mutations of MeCP2 alters expression and activity of the neurotransmitter gamma-amino butyric acid GABA. Reduced GABAergic signaling resulting from MeCP2 loss has significant effects on synaptic transmission in several brain regions important for respiratory control including the ventrolateral medulla. It has been previously observed that a reduction in inhibitory postsynaptic currents (IPSCs) in the ventrolateral medulla of Mecp2-null mice resulted from reduced levels of GABA and decreased expression of GABA receptor (GABAR). Therefore, another embodiment relates to a combination therapy for treating Rett syndrome including administering to a subject in need thereof an NMDAR antagonist, a GABAR agonist, and optionally a TrkB agonist and/or an agent modulates BDNF levels.

A GABAR agonist can include any agent that acts to directly or indirectly stimulate or increase the effect of the GABA receptor. Exemplary GABAR agonists can include but are not limited to GABA analogs, such as Neurontin (Gabapentin), PD-0200, 390 (atagabalin) and Lyrica (pregabalin).

GABAR agonists can also include gamma-amino butyric acid A (GABA-A) agonists, gamma-amino butyric acid B (GABA-B) agonists and/or combinations thereof. Exemplary GABA-A agonists for use in the present invention can be selected from the benzodiazepine groups acamprosate, barbiturates, ethanol, methaqualone, muscimol, nonbenzodiazepines (zaleplon, zolpidem, zopiclone), picamilon, progabide, and tiagabine. Exemplary GABA-B agonists can be selected from 4-Amino-3-(4-chlorophenyl)butanoic acid ((RS)-Baclofen), (R)-4-Amino-3-(4-chlorophenyl)butanoic acid ((R)-Baclofen), CGP35024, CGP44532, 3-Aminopropyl(methyl)phosphinic acid (SKF 97541), 1,4-Butanediol, GBL (γ-Butyrolactone), GHB (γ-Hydroxybutyric acid), GHV (γ-Hydroxyvaleric acid), GVL (γ-Valerolactone), lesogaberan, and phenibut.

The therapeutic agents described herein can be provided in pharmaceutical compositions for administration to a subject for the treatment of a pervasive develop disorder, such as Rett syndrome or autism spectrum disorder. In some embodiments, a pharmaceutical composition can include a therapeutically effective amount of an NMDAR antagonist alone and or in combination with a TrkB agonist, GABAR agonist, and/or agent that modulates BDNF levels and a pharmaceutically acceptable diluent or carrier. A combination therapy described herein can include the amount of a combination of therapeutic agents described herein effective to ameliorate biochemical and functional abnormalities associated with the pervasive development disorder.

In some embodiments, a therapeutically effective amount of an NMDAR antagonist can be an amount required to significantly improve at least one measure of forebrain function in a subject having Rett syndrome. A therapeutically effective amount of an NMDAR antagonist can be the amount required to reverse hypoactivity in forebrain circuits of subjects having Rett syndrome. In some embodiments, a therapeutically effective amount of an NMDAR antagonist can be the amount of an NMDAR antagonist required to reverse abnormal synaptic phenotypes in the cortex of subjects having Rett syndrome such as deficits in mTOR signaling, decreased density of dendritic spines and/or abnormal E/I balance. In a particular embodiment, a therapeutically effective amount of an NMDAR antagonist can be the amount required to significantly reverse brain activity deficits in subject with RTT. In another embodiment, a therapeutically effective amount of an NMDAR antagonist can be the amount required to inhibit apneic breathing in a subject with RTT and related disorders.

In some embodiments, a therapeutically effective amount of a TrkB agonist and/or agent that modulates BDNF levels can be the amount of a TrkB agonist and/or agent that modulates BDNF levels required to measurably increase BDNF expression in the brainstem of a subject, the amount of a TrkB agonist and/or agent that modulates BDNF levels required to measurably increase levels of TrkB phosphorylation in the brainstem of a subject, the amount required to acutely reverse synaptic hyperexcitability in brainstem respiratory and autonomic neural circuits in the subject, and/or the amount required to improve respiratory function in the subject, e.g., eliminate apneic breathing. In an exemplary embodiment, the administration of 50 mg/kg of LM22A-4 B.I.D for 4 weeks rescued wild-type levels of TrkB phosphorylation in the medulla and pons and restored wild-type breathing frequency in a subject.

In some embodiments, a therapeutically effective amount of a GABAR agonist can be the amount of a GABAR agonist required to measurably increase GABAergic signaling in a subject and/or the amount required to measurably increase synaptic transmission in brain regions important for respiratory control such as the ventrolateral medulla of a subject.

The therapeutic agents described herein are capable of further forming both pharmaceutically acceptable acid addition and/or base salts. All of these forms can be administered to the subject as part of a pharmaceutical composition for the treatment of a persuasive development disorder, such as Rett syndrome.

For preparing pharmaceutical compositions from the therapeutic agents of the present invention, pharmaceutically acceptable carriers can be in any suitable form (e.g., solids, liquids, gels, aerosols, etc.). Solid form preparations include, but are not limited to, powders, tablets, pills, capsules, cachets, suppositories, and dispersible granules. A solid carrier can be one or more substances which may also act as diluents, flavoring agents, binders, preservatives, tablet disintegrating agents, or an encapsulating material. The present invention contemplates a variety of techniques for administration of the therapeutic compositions. Suitable routes include, but are not limited to, oral, rectal, transdermal, vaginal, transmucosal, or intestinal administration;

parenteral delivery, including intramuscular, subcutaneous, intramedullary injections, as well as intrathecal, direct intraventricular, intravenous, intraperitoneal, intranasal, or intraocular injections, among others. Indeed, it is not intended that the present invention be limited to any particular administration route.

For injections, the agents may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

In powders, the carrier is a finely divided solid which is in a mixture with the finely dived active component. In tablets, the active component is mixed with the carrier having the necessary binding properties in suitable proportions, which has been shaped into the size and shape desired.

The powders and tablets can contain from five or ten to about seventy percent of the active compounds. Suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter and the like, among other embodiments (e.g., solid, gel, and liquid forms). The term "preparation" is intended to also encompass the formation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, in some embodiments of the present invention, a low melting wax, such as a mixture of fatty acid glycerides or cocoa butter; is first melted and the active compound is dispersed homogeneously therein, as by stirring. The molten homogenous mixture is then poured into convenient sized molds, allowed to cool, and thereby to solidify in a form suitable for administration Liquid form preparations include, but are not limited to, solutions, suspensions, and emulsions (e.g., water or water propylene glycol solutions). For parenteral injection, in some embodiments of the present invention, liquid preparations are formulated in solution in aqueous polyethylene glycol solution. Aqueous solutions suitable for oral use can be prepared by dissolving the active component in water and adding suitable colorants, flavors, and stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as tablets, capsules, and powders in vials or ampoules. Also, the unit dosage form can be a capsule, tablet, cachet, or lozenge itself, or it can be the appropriate number of any of these in packaged form.

General procedures for preparing pharmaceutical compositions are described in Remington's Pharmaceutical Sciences, E. W. Martin, Mack Publishing Co., PA (1990), which is herein incorporated by reference in its entirety.

The quantity of active component in a unit dose preparation may be varied or adjusted depending on the specific NMDAR antagonist administered according to the particular application and the potency of the NMDAR antagonist. For example, from 0.1 mg/kg per day to about 10 mg/kg of ketamine can be administered per dose every 24 hours, 36 hours, 48 hours, etc. The composition can, if desired, also contain other compatible therapeutic agents. It may be appropriate to administer the daily dose in the form of two or more sub-doses at appropriate intervals throughout the day.

The daily dosage of an NMDAR antagonist may be calculated daily during the administration periods of the intermittent closing regimen on the basis of the body weight or it may be calculated once at the start of each day during the administration periods. In some embodiments, the daily dosage of an NMDAR antagonist is calculated once at the beginning of each administration period. Alternatively the daily dosage of an NMDAR antagonist may also be calculated once at the start on one intermittent dosing regimen and remain unchanged during the two administration periods.

In particular embodiments, during the administration periods of the intermittent dosing regimen the quantity of an NMDAR antagonist in a unit dose preparation can be a subanesthetic dose. For example, the quantity of ketamine in a unit dose can be a sub-anesthetic dose ranging from about 1 mg/kg to less than 10 mg/kg per day. In a particular embodiment, the quantity of ketamine in a unit dose can be about 8 mg/kg per day. In another particular embodiment, the quantity of ketamine in a unit dose can be about 3 mg/kg per day. In other embodiments the quantity of the NMDAR antagonist remacemide in a unit dose can range from about 3 mg/kg to 120 mg/kg per day. In another exemplary embodiment, the quantity of a TrkB agonist LM22A-4 in a unit dose can range from about 50 mg/kg to 150 mg/kg per day.

The assessment of the clinical features and the design of an appropriate therapeutic regimen for the individual patient is ultimately the responsibility of the prescribing physician. It is contemplated that, as part of their patient evaluations, the attending physicians know how to and when to terminate, interrupt, or adjust administration due to toxicity, or to organ dysfunctions. Conversely, the attending physicians also know to adjust treatment to higher levels, in circumstances where the clinical response is inadequate, while precluding toxicity. The magnitude of an administrated dose in the management of the disorder of interest will vary with the severity of the condition to be treated, the patient's individual physiology, biochemistry, etc., and to the route of administration. The severity of the condition, may, for example, be evaluated, in part, by standard prognostic evaluation methods. Further, the dose and dose frequency will also vary according to the age, body weight, sex and response of the individual patient.

The following examples are included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims. All patents, patent applications, and publication cited herein are incorporated by reference in their entirety.

EXAMPLES

Figure 3:
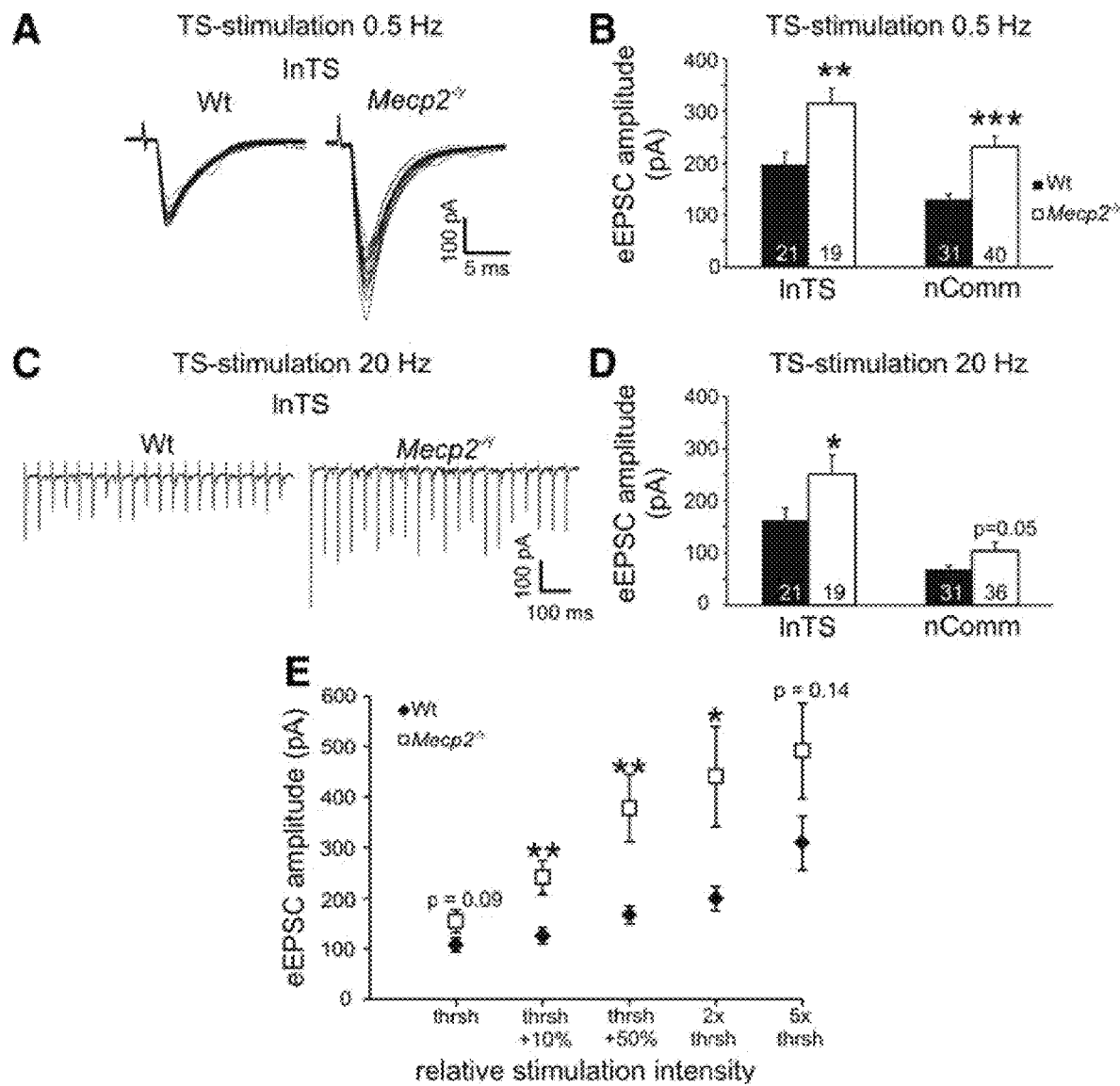
FIGS. 3A-E illustrate graphical representations of exaggerated evoked synaptic transmission in the adult Null 1 nTS and nComm. A, EPSCs evoked in the lnTS by low-frequency TS stimulation have significantly larger amplitudes in the Nulls compared with Wt. B, Statistical summary of genotype-dependent differences in eEPSC amplitudes in lnTS and nComm. C, Synaptic depression evoked by 20 Hz stimulus trains is unaffected by Mecp2 genotype. D, eEPSC amplitudes averaged across the entire 20 Hz stimulus train are significantly larger in the Null lnTS compared with Wt, with a similar trend in nComm. E, Input-output curve demonstrating that regardless of stimulus intensity, based on the individual neurons' stimulation response threshold, eEPSC amplitudes are larger in Nulls compared with Wt. *$p<0.05$; $p<0.01$; *$p<0.001$.

We discovered that NMDA receptor (NMDAR) targeted therapies have utility for symptom reversal in RTT. In direct support of the therapeutic potential of NMDAR antagonists for RTT, we showed that acute treatment of Mecp2 mutant mice with a sub-anesthetic dose of ketamine (8 mg/kg), a non-competitive NMDAR antagonist, completely reverses a subset of mutant endophenotypes, including hypoactivity in forebrain circuits and abnormal sensorimotor gating. These results are consistent with prior evidence that ketamine acutely increases forebrain network activity by disinhibiting cortical pyramidal cells. However, in addition to its acute effects on cortical network activity, ketamine also rapidly stimulates dendritic growth, BDNF translation and expression of key synaptic proteins through activation of mTOR signaling, which is deficient in Mecp2 mutants (FIG. 3).

These findings provide evidence that ketamine can effect long-term synaptic repair in RTT by enhancing structural and functional connectivity, as recently demonstrated in animal models of depression and stress. In fact, the antidepressant actions of low-dose ketamine are now attributed, at least in part, to these mTOR dependent effects on synaptic structure and function. We use mTOR activation, synaptic protein expression and synapse structure and function, in addition to behavior, as endpoints for measuring treatment efficacy in Mecp2 mutant mice.

Our finding that low-dose ketamine is effective at rescuing some abnormal phenotypes in Mecp2 mutants illustrate that ketamine may be an effective RTT therapeutic.

Example 1

Brain Activity Mapping in Mecp2 Mutant Mice Reveals Functional Deficits in Forebrain Circuits, Including Key Nodes in the Default Mode Network, that are Reversed with Ketamine Treatment In this example, we used Fos mapping, combined with electrophysiology, to compare activity patterns across the brain in wild-type (Wt) and Mecp2 mutant mice. Our data indicate marked and reproducible effects of the Mecp2 Null genotype on activity levels in different brain regions, including hyperexcitability in autonomic reflex pathways in the brainstem and hypoexcitability in key nodes of the default mode network in the forebrain. However, forebrain hypofunction can be reversed by treatment with a sub-psychotomimetic dose of ketamine, which also rescues behavioral dysfunction.

Materials and Methods

Animals: $Mecp2^{tm1.1Jae}$ mice were purchased from the Mutant Mouse Regional Resource Center (University of California Davis, Davis Calif.) and maintained on a mixed genetic background (129Sv, C57BL/6, BALB/c) by crossing $Mecp2^{tm1.1Jae}$ heterozygous females ($Mecp2^{-/+}$, Het) with $Mecp2^{tm1.1Jae}$ Wt males ($Mecp2^{+/y}$).

Immunohistochemistry
Tissue Preparation

Three- and 6-week-old male mice, or 11-week-old female mice, were deeply anesthetized by inhalation of isoflurane and perfused transcardially with PBS followed by ice-cold 4% paraformaldehyde in 0.1Mphosphate buffer, pH7.4, within 10 min. The kinetics of Fos protein induction and degradation are such that potential changes resulting from anesthesia would not be detectable within this timeframe. Brains were postfixed in 4% paraformaldehyde for 2.5 h, cryoprotected in 25% sucrose overnight, then frozen in 2-methylbutane at −45° C. and stored at −80° C. Coronal sections were cut at 40 μm with a cryostat microtome (Jung Frigocut 2800 N) and stored in PBS at 4° C.

Immunostaining

Free-floating 40 μm sections were processed for Fos immunostaining by blocking with 10% goat serum in dilution buffer (PBS, BSA, 0.3% Triton X-100) for 1.5 h and then incubated overnight at room temperature (20±2 h) in rabbit polyclonal anti-c-Fos primary antibody (1:3000, Calbiochem) in dilution buffer plus 10% goat serum. After sequential rinse steps in dilution buffer and PBS, sections were incubated in biotinylated goat anti-rabbit IgG secondary antibody (1:400, Vector Labs) in dilution buffer plus 15% goat serum for 1 h. After rinsing in PBS, sections were incubated in avidin and biotinylated horseradish peroxidase complex (ABC, 1:150, Vector Labs). Finally, sections were developed using the Sigma Fast diaminobenzidine and urea hydrogen peroxide set, mounted on Super Frost Plus slides and coverslipped using VectaShield (Vector Labs). Specificity of Fos immunolabeling was verified by demonstrating that preab sorption of the anti-c-Fos primary antibody with Fos peptide (Calbiochem) eliminated nuclear staining. To determine whether Fos-positive cells were neurons or astrocytes, a subset of sections were double stained with anti-c-Fos and either mouse anti-MAP2 (1:1000, Sigma) or mouse anti-GFAP (1:1000, Calbiochem), respectively. Regardless of genotype (Wt vs. Null), we only observed Fos labeling in neurons expressing the neuronal cytoskeletal protein MAP2 and saw no colocalization with the glial protein marker GFAP (glial fibrillary acidic protein) (n=2 animals per genotype). In addition, a subset of sections were double stained for Fos and either CaMKII (mouse anti-CaMKII, 1:10,000, Abcam), a marker for glutamatergic neurons, or parvalbumin (mouse anti-parvalbumin, 1:1500, Millipore), which is expressed by a subpopulation of GAB Aergic neurons. Alexa Fluor 488-conjugated goat anti-mouse secondary antibody (1:1000, or 1:2000 for CaMKII, Invitrogen) was used with each double stain.

Ketamine Injections

Animals were administered ketamine (8, 20, or 100 mg/kg, i.p.) or an equivalent volume of saline and then returned to their home cage for 90 min. Subsequently, the animals were deeply anesthetized by inhalation of isoflurane, perfused transcardially, and processed for Fos staining as described above.

Data Analysis

Sections were visualized and photographed using an AxioSkop2 microscope (Zeiss) equipped with a Quantifire XI microscope camera (Optronics). Fos positive cells were counted using point by-point analysis with Neurolucida software (MBF Bioscience). Before analysis, the photomicrographs were coded so that the observers were blinded to the genotype. Cells were counted in every third section through the nTS, and in a representative subset of sections through the other brain regions analyzed. All sections were analyzed twice by two independent and blinded observers, and respective counts were averaged. The nTS was sampled at 12 levels through the rostro-caudal extent of the nucleus and the average counts at each level were then added together to estimate the total number of labeled cells per animal. To define genotype effects on Fos expression, G*Power 3 power analysis software was used to determine group sizes.

Electrophysiology Slice Preparation

Horizontal brainstem slices were prepared from 3- and 5- to 7-week-old Mecp2 Null and Wt male mice. Animals were deeply anesthetized by inhalation of isoflurane and then decapitated. Brains were removed from the skull and placed in low $Ca^{2+}$, ice-cold artificial CSF (ACSF) containing the following (in mM): 125 NaCl, 3 KCl, 1.2 $NaH_2PO_4$, 1 $CaCl_2$, 1.2 $MgSO_4$, 2 $MgCl_2$, 25 $NaHCO_3$, 10 D-glucose, and 0.4 L-ascorbic acid, equilibrated to pH 7.4 with 95% $O_2$/5% $CO_2$, for 2-5 min. Then, brainstems were dissected, glued on the mounting platform of a vibratome (Leica, Vt. 1000S), and horizontal sections containing the nucleus tractus solitarius (nTS), including a long segment of the tractus solitarius (TS) were cut at 220-250 μm. Slices were then transferred to recording ACSF (containing in mM: 125 NaCl, 3 KCl, 1.2 $NaH_2PO_4$, 2 $CaCl_2$, 1.2 $MgSO_4$, 25 $NaHCO_3$, 10 D-glucose, and 0.4 L-ascorbic acid, equilibrated to pH 7.4 with 95% $O_2$/5% $CO_2$) at ~32° C. and allowed to recover from the procedure for at least 30 min before recordings.

Recordings

Slices were placed into the recording chamber, held in place with nylon-wired grid and superfused with recording ACSF at 30-32° C. at a flow rate of 4-5 ml/min. For stimulation of presynaptic inputs to nTS neurons, a concentric bipolar stimulation electrode (Frederick Haer) was placed on the TS, the medullary tract containing the central axons of cardiorespiratory and other primary afferent inputs to the brainstem, rostral to recording sites. Patch pipettes were pulled from thick-walled borosilicate glass capillaries, and filled with intracellular solution (containing in mM: 130 K_gluconate, 10 NaCl, 11 EGTA, 1 $CaCl_2$, 10 HEPES, 1 $MgCl_2$, 2 MgATP, 0.2 NaGTP), had resistances between 4 and 7MΩ. Recordings were made within 2 regions of nTS at the level of, and caudal to the obex: (1) lateral to or within the TS, including the interstitial, lateral and ventrolateral subnuclei [referred to as lateral nTS (lnTS)], (2) within the commissural subnucleus (nComm). Neurons were visualized with an upright Olympus microscope (BX51WIF). Cells were identified as second-order neurons if they received monosynaptic input, defined as a low jitter of latency of evoked postsynaptic responses (<250 μs), at 0.5 Hz TS stimulation. Evoked, spontaneous and miniature EPSCs (eEPSCs, sPSCs, mEPSCs) were recorded from cells meeting this criterion in the whole-cell voltage-clamp configuration at a holding potential of −60 mV. To record eEPSCs, the TS was stimulated at 0.5 and 20 Hz. In a subset of nComm neurons, input-output curves were obtained by gradually increasing the stimulus intensity based on the neurons' individual threshold (thrsh, thrsh+10%, thrsh+50%, 2×thrsh, 5×thrsh). In all other experiments the stimulation intensity was set to threshold+10%, typically between 50 and 200 μA (stimulus duration 100 μs, 20 sweeps). To compare intrinsic neuronal excitability between genotypes, action-potential properties and firing frequency in response to current injection (50 pA increments) were recorded in nComm neurons as well. Only neurons with a resting membrane potential of at least −40 mV upon breakthrough were accepted. Data were acquired using pClamp software. Signals were amplified (Axopatch 200B, Molecular Devices), filtered at 2 kHz and digitized at 10 kHz.

Data Analysis

Spontaneous and evoked postsynaptic currents were analyzed with Clampfit and Microsoft Excel. In the analysis of eEPSCs, 20 sweeps were averaged with Clampfit and the resulting eEPSC amplitudes were measured and compared between genotypes at different stimulation intensities. For sPSCs and mEPSCs, traces were digitally filtered at 1 kHz, events were counted within 2 min segments, and instantaneous frequencies and amplitudes were analyzed. The detection threshold for sPSCs and mEPSCs was set as 1-1.5× peak-to-peak noise. Miniature EPSC rise time was analyzed as the time from onset to peak of individual events, and the decay time was estimated as the time between peak and recross of the detection threshold.

Prepulse Inhibition

Prepulse inhibition (PPI) of the acoustic startle response (ASR) was measured to assess sensorimotor gating function using Med Associates Startle Response recording system. Mice were divided into four groups (Het ketamine, Het vehicle, Wt ketamine, Wt vehicle), and received injections of either ketamine (8 mg/kg) or an equivalent amount of saline immediately before they were placed individually inside a small-sized, nonrestrictive, cubical Plexiglas recording chamber [2.5 inches (L)×2.5 inches (W)×1.75 inches (H)] fixed on an accelerometer platform and allowed to acclimate for 5 min. Subsequently, the mouse was exposed to 4 testing blocks. In the first testing block, the initial startle response amplitude was determined by delivering a 40 ms pulse of 120 dB broadband white noise and recording the maximum startle amplitude (Vmax). A baseline startle response was determined by repeating this recording paradigm for six consecutive trials (with 8-23 s between each stimulus) and calculating the average Vmax measured in those trials. In the second and third testing blocks, the mice were exposed to a series of "pulse-only" or "prepulse-pulse pair" stimuli to determine the effect that a reduced intensity prepulse had on the acoustic startle response. The pulse-only stimulus consisted of an 80 ms stimulus of 120 dB. The prepulse-pulse pair trials were conducted by delivering a single 20 ms prepulse, with an intensity of 73, 76 or 82 dB before an 80 ms stimulus with an intensity of 120 dB. An average delay of 15 s (8-23 s) occurred between each stimulus. Each prepulse-pulse pair trial was repeated 10 times, pulse only trials were repeated 12 times. The Vmax measured from each prepulse-pulse trial was compared with the Vmax measured from the 120 dB pulse-only trials, and a percentage prepulse inhibition (% PPI) was calculated for each prepulse intensity. In the fourth testing block, startle response Vmax was recorded from 6 additional 40 ms pulses of 120 dB broadband white noise (with 8-23 s between each stimulus) and compared with the baseline startle response from the first testing block to eliminate the possibility of habituation to the acoustic stimulus throughout the test.

Statistical Analysis

All data are presented as means±SEM. Genotype-dependent differences were analyzed by unpaired two-tailed Student's t test. Multiple group data were analyzed by one-way ANOVA with post hoc least significant difference (LSD) test for intergroup comparisons. Miniature EPSC frequency and amplitude distributions were compared with the Kolmogorov-Smirnov test. Results were considered significant if the p value was <0.05.

Results

Fos Expression is Markedly Altered in the Mecp2 Null Brain Compared with Wt Controls Fos immunostaining has been widely used as a surrogate marker of neuronal depolarization to map circuits and pathways in the normal brain that are activated by specific types and patterns of neural stimulation. Given that excitatory-inhibitory imbalance has been documented within various cell groups in the Mecp2 mutant brain, we hypothesized that Wt and Null animals would exhibit regional differences in Fos expression and that these differences could be used to map sites of circuit dysfunction in the Null brain. To address this possibility, we initially surveyed Fos expression in serial sections throughout the rostro-caudal extent of the brain, from the olfactory bulbs to the spinomedullary junction, in Wt and Null mice at 3 and 6 weeks of age, i.e., before and after the appearance of overt RTT-like symptoms. We found no obvious effect of Mecp2 genotype on the number of Fos-positive neurons in 3-week-old animals in any brain region examined (postnatal day 21±3; Null, N=4; Wt, n=4). However, there were marked and reproducible differences between Null and Wt animals at 6 weeks of age across the neuraxis (postnatal day 42±3; Null, n=5-7; Wt, n=5-7; Table 1).

Forebrain

The most dramatic effects of Mecp2 genotype on Fos expression were observed in cortical and subcortical limbic structures, including the prelimbic and infralimbic cortices, retrosplenial cortex, cingulate cortex, the nucleus accumbens (nAC, both core and shell), as well as the piriform cortex, the motor cortex and lateral septal nuclei, all of which showed significantly less Fos labeling in Null animals compared with Wt (FIG. 1; Table 1). A similar pattern was observed in the auditory, somatosensory, and primary visual cortices, as well as the caudate/putamen. In cortical regions, genotype effects on Fos labeling did not appear to exhibit any laminar specificity. Quantitative analysis revealed that the number of Fos-positive cells in Nulls was reduced by up to 80% compared with Wt (% Wt; piriform cortex, 46.6%; nAC, 23.4%; cingulate cortex, 29.4%; retrosplenial cortex, 18.6%; prelimbic cortex, 24.3%; infralimbic cortex, 26.3%; motor cortex, 15.6%; lateral septal nucleus, 32.9%; Table 1). No genotypic differences in Fos expression were noted in other forebrain regions, such as the hippocampus, including the dentate gyrus and the CA1 and CA3 regions together (CA; Table 1) nor in the mammillary bodies, thalamus and hypothalamus.

Brainstem and Cerebellum

Figure 2:
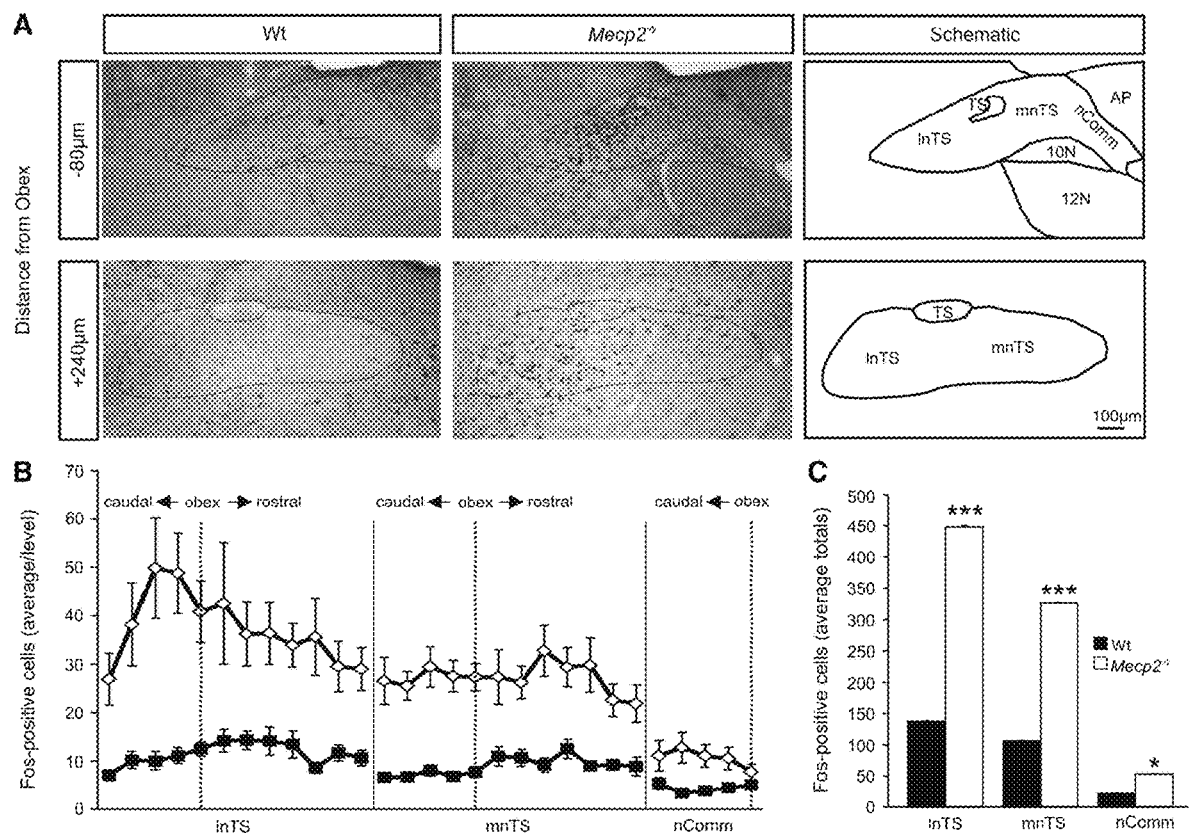
FIGS. 2A-C illustrate photomicrographs and graphical illustrations showing increased Fos expression in the hindbrain nTS in symptomatic Mecp2 Null mice. At 6 weeks of age, Null mice exhibit markedly increased levels of Fos expression in subnuclei within the nucleus tractus solitarius (nTS) of the medulla. A, Photomicrographs of representative coronal sections through nTS at 2 different rostrocaudal levels, with a schematic overlay illustrating nTS subnuclei and landmarks. B, Quantitative analysis of genotype-dependent differences in Fos expression across the entire rostrocaudal extent of the lnTS, mnTS, and nComm subnuclei of nTS in increments of 80 µm. Note that except for the most anterior and posterior sections through nComm, Fos expression is significantly elevated throughout the rostrocaudal extent of the Null nTS compared with Wt ($p<0.05$). Dotted lines mark the obex. C, Average counts of Fos-positive cells at each level were combined to provide an estimate of the absolute total number of Fos-positive cells throughout the rostrocaudal extent of nTS in Null vs. Wt. 10N, Dorsal motor nucleus of vagus; 12N, hypoglossal nucleus; AP, area postrema; lnTS, lateral nTS; mnTS, medial nTS; nComm, commissural nTS; TS, tractus solitarius. *$p<0.05$; ***$p<0.001$.

In the brainstem, the periaqueductal gray (PAG) and the nucleus of the solitary tract (nTS), both of which are major cell groups involved in modulation of autonomic homeostasis exhibited the strongest genotype dependent differences in Fos expression levels. Specifically, the Null PAG had significantly fewer Fos-positive cells compared with Wt (Wt, 38.1±20.0; Null, 25.1±6.0; p<0.01; Table 1; FIG. 1F). This was due primarily to a deficit in the ventral subdivision (v1PAG, reduction of 35.5%; Table 1), whereas Fos-expression was not significantly different between Wt and Null in the lateral (1PAG) and dorsal divisions (dPAG), despite strong trends toward lower expression in the Nulls (Table 1). In contrast, Null mice exhibited significantly more Fos-positive cells throughout the rostrocaudal extent of the three major cardiorespiratory subnuclei in nTS [medial (mnTS), commissural (nComm) and lateral nTS, including interstitial, lateral and ventrolateral subnuclei (lnTS)] compared with Wt (% Wt; mnTS; 306.5%; nComm; 245.0%, lnTS; 324.8%; FIG. 2A-C; Table 1). However, no significant genotype-dependent effects were found in the nucleus retroambiguus (nRA), the preBotzinger complex (pBC), pontine nucleus, or the cerebellum (Table 1).

TABLE 1

Quantification of Fos expression in selected brain regions in Null vs. Wt mice

|  | Male Wt | Mall Null |
| --- | --- | --- |
| Medulla | n = 7 | n = 7 |
| Medial nTS | 106.5 ± 0.5 | 326.4 ± .09*** |
| Lateral nTS | 137.9 ± 0.7 | 447.9 ± 2.0*** |
| Commissuraln TS | 21.8 ± 0.2 | 53.4 ± 0.5* |
| Nucleus retroambiguus | 7.9 ± 1.2 | 11.9 ± 2.2# |
| preBotzinger Complex | 23.6 ± 7.4 | 29.1 ± 4.7 |
| Pons | n = 5 | n = 5 |
| Pontine nucleus | 322.7 ± 63.7 | 199.4 ± 51.5 |
| Midbrain | n = 5 | n = 5 |
| Dorsal PAG | 21.6 ± 32.8 | 13.9 ± 4.7 |
| Lateral PAG | 53.0 ± 25.2 | 35.9 ± 10.7# |
| Ventral PAG | 39.7 ± 12.3 | 25.6 ± 7.5* |
| Forebrain | n = 5 | n = 5 |
| Piriform cortex | 266.3 ± 35.0 | 124.2 ± 19.7* |
| Nucleus accumbens | 114.4 ± 22.8 | 26.8 ± 7.9** |
| Cingulate cortex | 50.4 ± 13.08 | 14.8 ± 4.8* |
| Retrosplenial cortex | 39.7 ± 10.86 | 7.4 ± 1.6* |
| Prelimbic cortex | 34.6 ± 6.81 | 8.4 ± 3.6** |
| Infralimbic cortex | 26.6 ± 3.8 | 7.0 ± 2.2** |
| Motor cortex | 19.9 ± 3.8 | 3.1 ± 1.6** |
| Lateral septal nucleus | 48.6 ± 14.9 | 11.6 ± 4.9* |
| Hippocampus (CA1 + CA3) | 22.5 ± 8.3 | 14.0 ± 4.6 |
| Hippocampus (DG) | 14.3 ± 4.7 | 9.5 ± 2.6 |

Data are displayed as mean ± SEM (*<0.05; p < 0.01; *p < 0.001; #p < 0.15)

Figure 4:
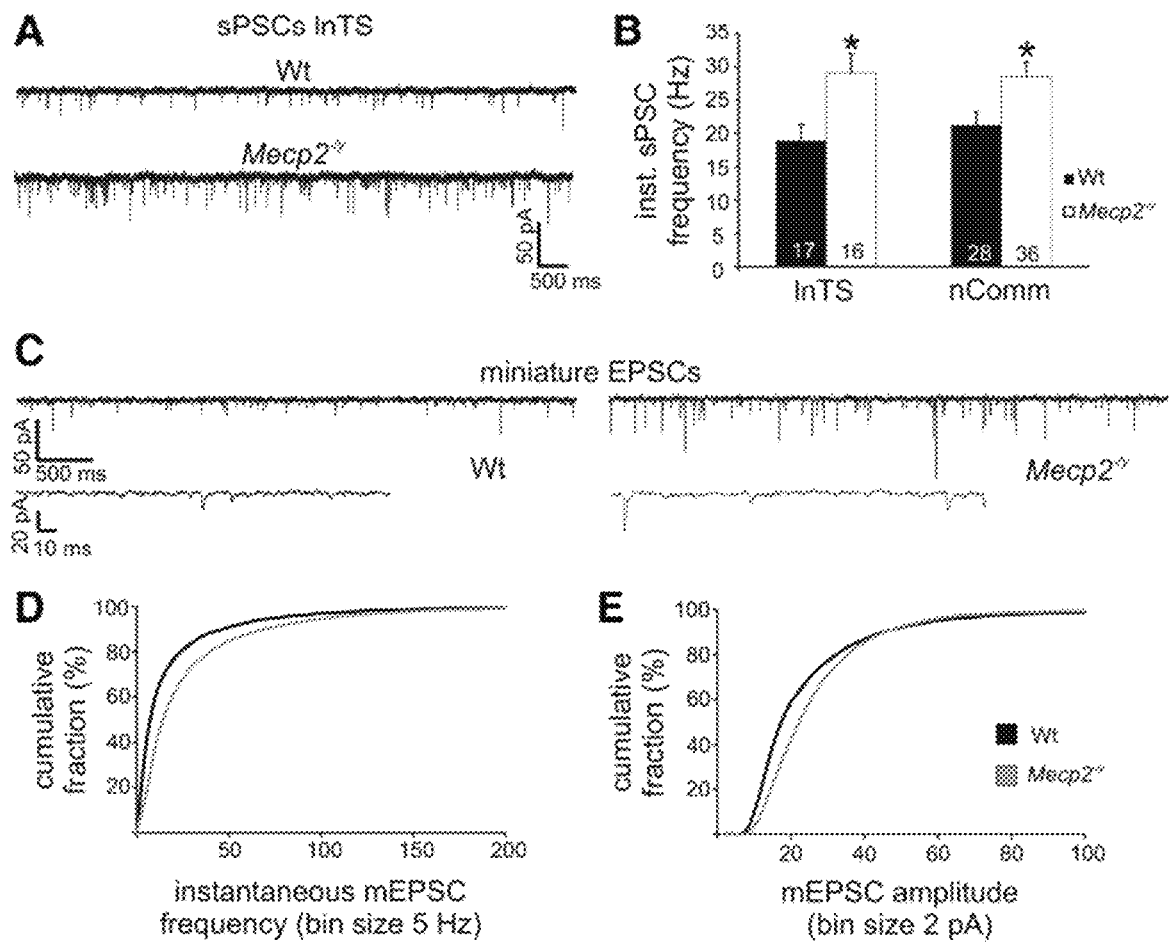
FIGS. 4A-E illustrate graphical representations of enhanced spontaneous excitatory currents at primary afferent synapses in the Null nTS compared with Wt. A, Representative recordings from a Wt and a Null 1 nTS second-order neuron illustrating higher sPSC frequency in the Nulls. B, Group data reveal a significantly higher sPSC frequency in both Null lnTS and nComm compared with Wt. C, Representative recordings from a Wt and a Null 1 nTS second order neuron at low (top traces) and high (bottom traces) resolution illustrating higher mEPSC frequency and amplitudes in the Nulls. D, E, Cumulative mEPSC frequency (D) and amplitude (E) distribution curves from recordings of 1 nTS and nComm neurons show right-shifts in the Nulls, indicating higher mEPSC frequencies and amplitudes, respectively, compared with Wt. *$p<0.05$; $p<0.01$; *$p<0.001$.

Genotype Effects on Fos Labeling are Associated with Altered Synaptic Excitability Although Fos has been widely validated as a marker of neural activity in normal animals, this has not previously been analyzed in animals lacking MeCP2. Therefore, to determine whether or not Mecp2 genotype effects on Fos labeling indeed reflect differences in neural activity, patchclamp electrophysiological recordings were used to compare synaptic and neuronal excitability in Wt and Null mice at 5-7 weeks of age, using the nTS as a model system. The nTS is ideally suited for such analyses because of a clear anatomic segregation between presynaptic inputs in the solitary tract (TS) and second-order neurons within the various nTS subnuclei. Indeed, EPSC amplitudes evoked by TS stimulation at 0.5 Hz (20 sweeps; stimulation intensity at 10% above the neurons' individual thresholds) were significantly larger in Nulls compared with Wt in both the lnTS and nComm (lnTS; Null, 314.1±29.3 pA, n=19; Wt, 198.1±22.7 pA, n=21; p<0.01, unpaired Student's t test; nComm; Null, 231.5±21.1 pA, n=40; Wt, 129.3±11.2 pA, n=31; p<0.001; FIG. 3A,B), consistent with previous findings in the mnTS. To validate these genotypedependent differences and to facilitate comparisons across individual neurons and between genotypes, threshold-based input-output curves were recorded from a subset of nComm neurons at 0.5 Hz TS stimulation. These recordings revealed significantly higher eEPSC amplitudes in the Null nComm at the 3 intermediate stimulation intensities and strong trends at the lowest and highest stimulation intensities (Wt, n=17; Null, n=16; FIG. 3E). Increasing TS-stimulation frequency to 20 Hz also revealed significantly larger eEPSC amplitudes in the Null lnTS, and a strong trend in nComm as well (lnTS; Null, 251.8±35.7 pA; Wt, 162.6±23.2 pA, p<0.05; nComm; Null, 103.6±16.3 pA; Wt, 68.7±6.5 pA, p<0.052; FIG. 3C,D). Frequency-dependent synaptic depression, a feature of primary afferent synapses in nTS was unaffected by Mecp2 genotype in either nComm or lnTS. Similarly, basic membrane properties, including membrane potential (Vm), membrane capacitance (Cm) and membrane resistance (Rm) were comparable between genotypes (Tables 2, 3) Likewise, action-potential properties were similar between the genotypes, and current-induced step depolarization at −60 mV evoked comparable numbers of APs at all current levels except for 50 pA (the lowest level tested) which evoked fewer APs in Null cells compared with Wt (Tables 4, 5). To define potential genotype effects on spontaneous network activity in nTS, sPSCs were recorded and analyzed in 2 min intervals. In the lnTS, we detected significantly more events in Nulls compared with Wt (Null, 1165.3±169.3, n=16; Wt, 718.1±141.6, n=17, p<0.05) which resulted in a significantly higher instantaneous frequency (Null, 29.0±3.1 Hz; Wt, 18.9±2.4 Hz, p<0.05; FIG. 4A,B). Instantaneous sPSC frequency was also increased in the Null nComm compared with Wt (Null, 28.4±2.3 Hz, n=36; Wt, 21.2±2.1 Hz, n=28, p<0.05; FIG. 4B), in association with a strong trend toward an increase in the number of spontaneous events (Null, 1231.9_160.8; Wt, 867.2±127.3; p<0.08). Addition of the AMPA-receptor blocker 6-cyano-7-nitroquinoxaline-2,3-dione to the superfusate (10 μM) completely abolished sPSCs and reduced eEPSC amplitudes by 92.2±1.4% (n=10), indicating that primary afferent transmission in nTS is mainly mediated by AMPA-receptors. To specifically examine how Mecp2 genotype may affect spontaneous presynaptic release of excitatory transmitter, miniature EPSCs were recorded in the presence of bicuculline (10 μM) and TTX (0.5 μM) and analyzed in 2 min intervals. Since we found similar genotype effects in the nComm and lnTS, data from both subnuclei were pooled. In Nulls, both the number of events and the instantaneous mEPSC frequency were significantly increased compared with Wt (Null, 1006±162.6 events, 24.6±2.9 Hz, n=9; Wt, 461.6±94.0 events, 15.9±2.4 Hz, n=7; p values <0.05; FIG. 4C, D). Accordingly, the cumulative frequency distribution curve showed a significant right shift in the Nulls (Kolmogorov-Smirnov test, p<0.05, FIG. 4D). Moreover, the cumulative mEPSC amplitude distribution curve also displayed a significant right shift in the Nulls, indicating larger mEPSC amplitudes (Kolmogorov-Smirnov test, p<0.05, FIG. 4E). We did not observe genotype differences in mEPSC rise or decay times (rise time; Wt, 1.00±0.11 ms; Null, 0.91±0.09 ms; decay time; Wt, 2.91±0.49 ms; Null, 2.75±0.36 ms).

Elevated Fos Expression and Synaptic Hyperexcitability Develop in Parallel in Mecp2 Nulls Analysis of 6-week-old animals revealed a strong association between elevated Fos expression and synaptic hyperexcitability within specific subnuclei in the Null nTS compared with Wt. To further explore how these two endophenotypes may be linked to each other, and to the onset of disease, we quantified Fos levels and analyzed synaptic excitability in the nTS of 3 week-old mice before the appearance of overt symptoms. In contrast to 6-week-old animals, Fos was expressed at relatively low levels in the nTS of both Null and Wt animals at 3 weeks, and we saw no significant effect of genotype in any subnucleus of the nTS (Wt, n=4; Null, n=4; mnTS; Wt, 3.8±0.5 cells; Null, 3.5±0.4 cells; lnTS; Wt, 4.4±0.7 cells; Null, 3.7±0.7 cells; nComm; Wt, 3.1±0.5 cells; Null, 1.9±0.2 cells). To evaluate genotype effects on synaptic function in nTS at 3 weeks of age, we focused our analysis on the lnTS. With the exception of $V_m$, which was more negative in Wt neurons, there was no effect of genotype on basic neuronal properties (Table 2).

TABLE 2

Membrane properties of second-order nTS relay neurons (lnTS)

| | Juvenile lnTS | | Adult lnTS | |
| --- | --- | --- | --- | --- |
| | Wt (n = 26) | Null (n = 30) | Wt (n = 21) | Null (n = 18) |
| $V_m$ (mV) | −64.5 ± 2.1 | −59.5 ± 1.4 | −60.4 ± 1.8 | −62.9 ± 2.6 |
| $C_m$ (pF) | 37.8 ± 2.4 | 36.8 ± 2.7 | 34.6 ± 3.0 | 29.9 ± 1.9 |
| $R_m$ (MΩ) | 440.6 ± 60.0 | 462.0 ± 75.0 | 447.3 ± 56.3 | 464.5 ± 51.5 |

Data are displayed as mean ± SEM;
*p < 0.05

Figure 5:
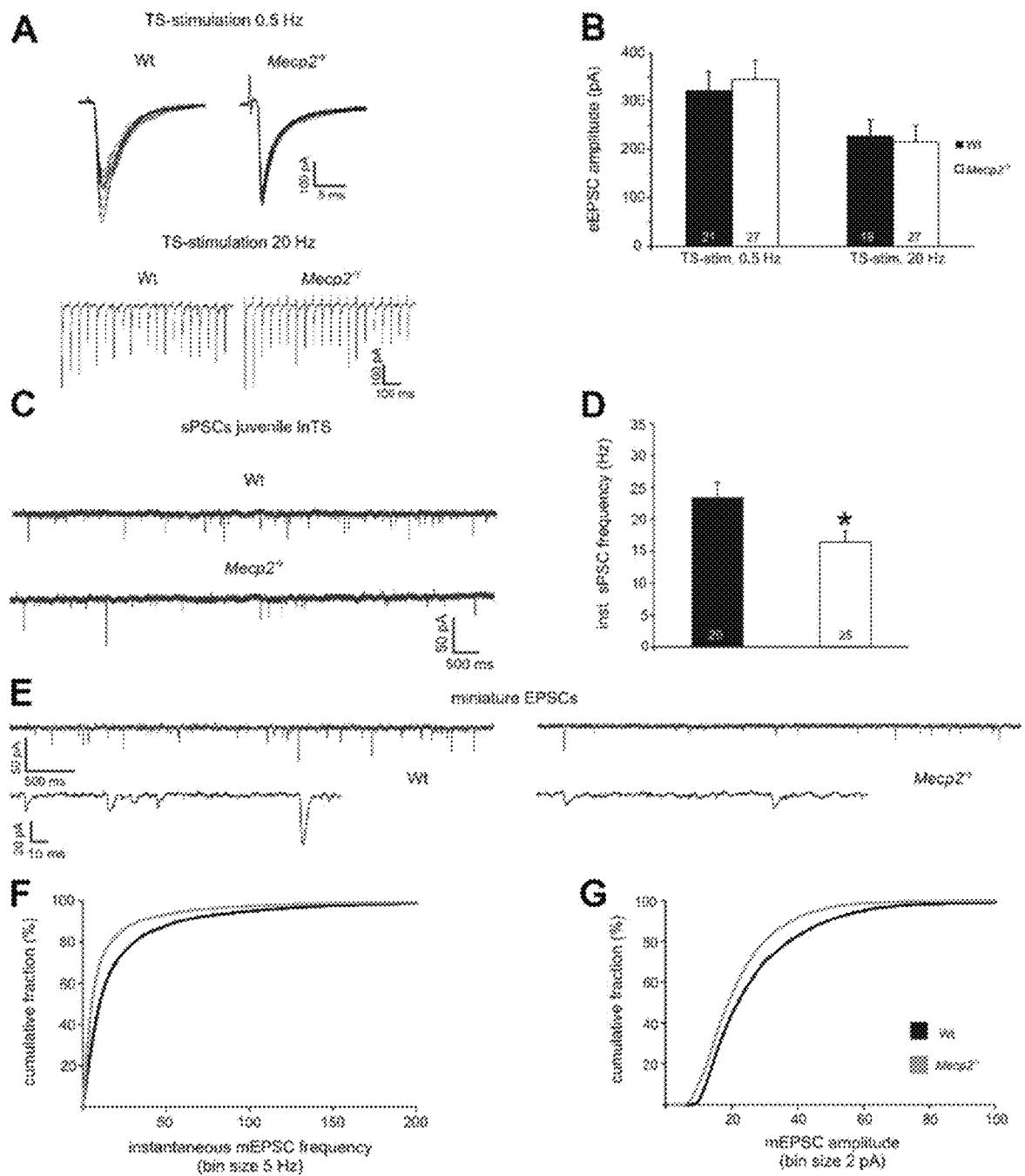
FIGS. 5A-G illustrate graphical representations of evoked synaptic transmission is normal in the Null nTS at 3 weeks of age despite reduced spontaneous excitatory currents. A, B, 0.5 and 20 Hz stimulation both yield similar EPSC amplitudes in juvenile Wt and Null 1 nTS second-order neurons. C, D, Spontaneous PSC frequency is lower in juvenile Null 1 nTS neurons compared with Wt. E, Raw traces illustrating reduced mEPSC frequency and amplitudes in the Nulln TSat 3 weeks. F, G, Cumulative mEPSC frequency (F) and amplitude (G) distribution curves demonstrate left shifts in the Nulls at 3 weeks, indicating lower mEPSC frequencies and lower amplitudes, respectively, compared with Wt. *$p<0.05$; $p<0.01$; *$p<0.001$.

Similarly, there was no effect of genotype on eEPSC amplitudes evoked by TS stimulation at 0.5 Hz (Wt, 322.8±38.2 pA, n=21; Null, 344.4±41.2 pA, n=27; FIG. 5A, B) or 20 Hz (Wt, 228.5±34.1 pA; Null, 215.9±33.3 pA; FIG. 8A, B). Regardless of genotype, eEPSC amplitudes at 3 weeks of age were comparable to those recorded in Nulls at 6 weeks (see above). Instantaneous sPSC frequency (Wt, 23.4±2.4 Hz, n=20; Null, 16.4_1.7 Hz, n 25, p<0.05) and number of events (Wt, 877.6±123.2; Null, 545.0±81.0, p<0.05) were significantly lower in juvenile Nulls compared with juvenile Wt (FIG. 8C,D). To compare the spontaneous release of excitatory transmitter between the genotypes in presymptomatic mice in more detail, we constructed mEPSC frequency and amplitude probability distribution plots. In contrast to mEPSC analyses from 5- to 7-week-old mice, both frequency and amplitude distribution plots showed a significant left shift in the Nulls (Kolmogorov-Smirnov test, p<0.05; Wt, n=8; Null, n=9; FIG. 8E-G), indicating lower mEPSC frequency and smaller mEPSC amplitudes. Miniature EPSC rise and decay times were comparable between the genotypes (rise time; Wt, 0.86±0.08 ms; Null, 0.79±0.09 ms; decay time; Wt, 1.96±0.15 ms; Null, 2.04±0.17 ms).

Figure 6:
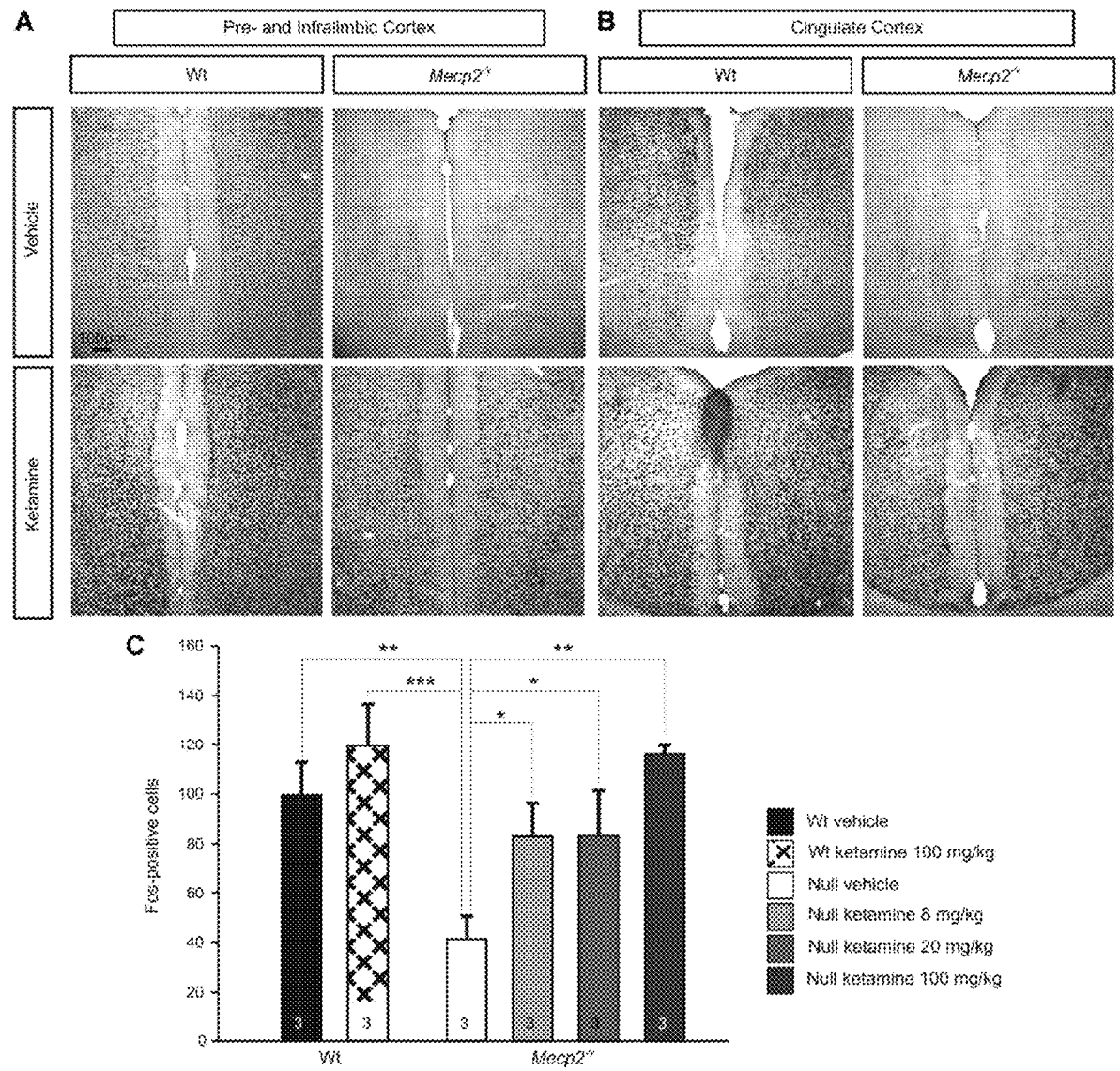
FIGS. 6A-C illustrate photomicrographs and graphical illustrations illustrating systemic treatment with ketamine acutely increases Fos expression in the forebrain of Wt and Null mice and reverses the Fos-deficient phenotype in Nulls. A, B, Injection of ketamine (100 mg/kg, i.p.) increases Fos expression throughout the forebrain in Nulls and Wt; representative sections from the prelimbic and infralimbic cortices (A) and cingulate cortex (B) are shown. C, Ketamine causes a dose-dependent increase in Fos expression levels in Null mice, restoring Fos expression to naive Wt levels as shown here in the piriform cortex. In Wt, 100 mg/kg ketamine increased the number of Fos-positive cells by 20%. *$p<0.05$; $p<0.01$; *$p<0.001$.

The NMDA Receptor Antagonist Ketamine Restores Wt Levels of Fos Expression in the Null Forebrain To determine whether or not decreased Fos expression in cortical structures within the adult Null forebrain reflects an intrinsic inability to express Fos in the absence of MeCP2 or, alternatively, results from reduced network activity, we compared the effects of ketamine treatment in Null and Wt mice. Ketamine is an NMDA receptor antagonist that has previously been shown to upregulate Fos expression in the limbic forebrain of mice and rats by disinhibiting cortical pyramidal cells. Indeed, acute treatment with ketamine (8 mg/kg, 20 mg/kg, 100 mg/kg, i.p.) markedly increased Fos labeling within 90 min of injection in both Wt and Null animals compared with saline-injected controls (n=3 for each group, FIG. 6). In both genotypes, Fos induction was strongest in the prelimbic, infralimbic, piriform, cingulate and retrosplenial cortices (FIG. 6). Quantitative analysis of Fos labeling in the piriform cortex revealed a dosedependent effect of ketamine on the number of Fos-positive cells in the Nulls, including restoration of Wt levels at higher doses (Null vehicle, 41.3±9.2 cells; Null 8 mg/kg ketamine, 82.9±_13.4 cells; Null 20 mg/kg ketamine, 83.2±18.2 cells; Null 100 mg/kg ketamine, 116.3±26.4 cells; Wt vehicle, 99.5±13.3 cells; Wt 100 mg/kg ketamine, 119.3±17.2 cells; FIG. 6C). These data indicate that although Fos is down-regulated in limbic forebrain structures in the absence of MeCP2, Fos expression remains plastic and subject to induction by factors that alter forebrain network activity.

Ketamine Rescues Abnormal PPI of Acoustic Startle in Mecp2 Hets

Figure 7:
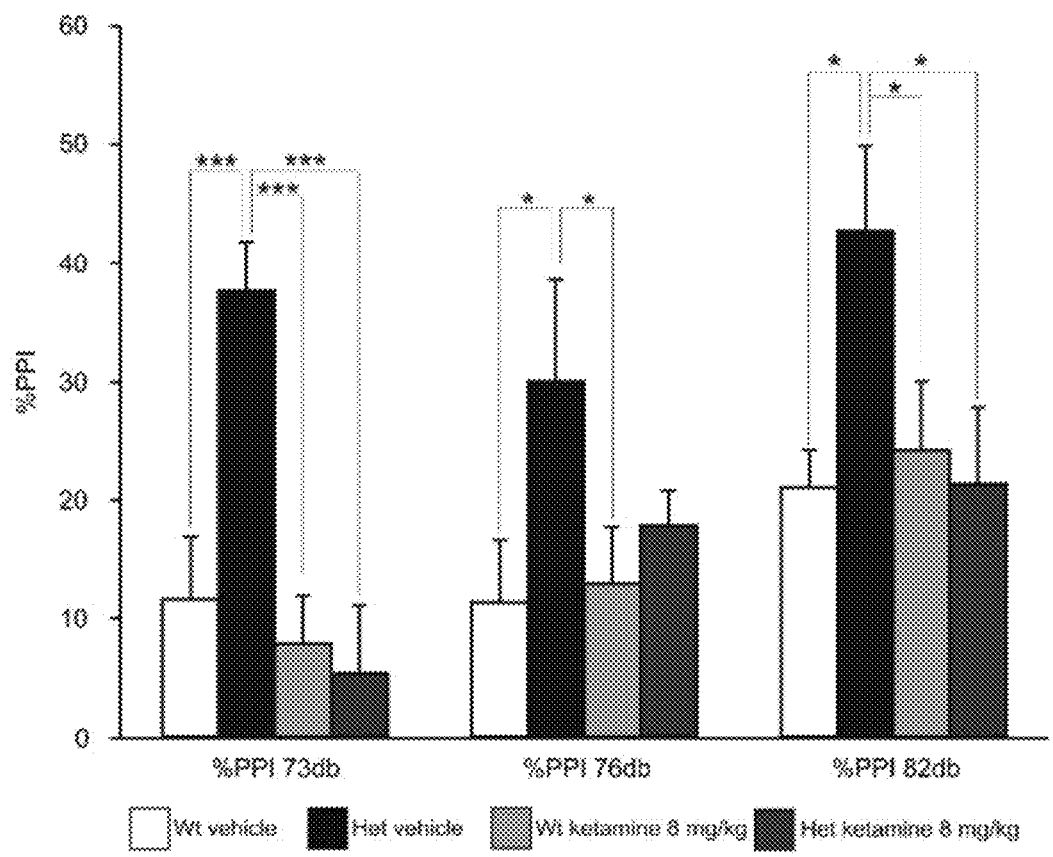
FIG. 7 illustrates a graphical illustration of Het mice exhibit abnormal prepulse inhibition of acoustic startle which is restored to Wt levels by acute treatment with a sub-psychotomimetic dose of ketamine. Het mice exhibit a significant increase in PPI amplitude at 11 weeks of age that is restored to Wt levels by acute treatment with ketamine at 8 mg/kg. *$p<0.05$; ***$p<0.001$.

PPI of the ASR is a measure of sensorimotor gating and is widely used as an index of cognitive function in neuropsychiatric disorders, including ASDs. PPI measures the ability of a weak sensory input to modulate behavioral responses to a subsequent strong sensory stimulus and thereby reflects the function of inhibitory circuitry thought to be critical for normal cognition. Because the circuitry underlying PPI includes structures that exhibit reduced Fos staining in Nulls, such as the mPFC and nAC and because ketamine treatment of Nulls rescues Fos expression in these regions, we decided to use PPI as an index of forebrain circuit function in the absence and presence of ketamine. Heterozygous female Mecp2 mutants (Hets) were used for these experiments because acoustic startle measurements can be unreliable in Nulls due to their relatively small size. Although, as described by others, overall levels of Fos expression are lower in females compared with males, Fos was significantly reduced in the Het forebrain compared with Wt, as in male Nulls (Table 3). PPI was compared in vehicle- and drug-treated Hets and age and sex-matched Wt animals, using a sub-psychotomimetic dose of ketamine (8 mg/kg; n=9 for Wt vehicle and ketamine, n=8 for Het vehicle and ketamine). Vehicle-treated Hets exhibited a significant increase in PPI amplitude compared with vehicle treated Wt at all levels of prepulse tested (% PPI 73 dB; Wt, 11.5±5.3, Het, 37.6±4.1, p<0.001; % PPI 76 dB; Wt, 11.3±5.2, Het, 29.9±8.6, p<0.05; % PPI 82 dB; Wt, 20.9±3.2, Het, 42.6±7.1, P<0.05; FIG. 7). Acoustic startle by itself was not different among groups (Startle amplitude; Wtvehicle, 974.8_109.8; Het vehicle, 759.6±73.7). Acute treatment with ketamine restored PPI in Hets to Wt levels (Het ketamine, % PPI 73 dB, 5.3±5.8; % PPI 76 dB, 17.8±2.9; % PPI 82 dB, 21.4±6.4, FIG. 7), whereas ketamine treatment did not alter PPI in Wt (Wt ketamine, % PPI 73 dB, 7.8±4.1; % PPI 76 dB, 12.8±4.8; % PPI 82 dB, 24.1±5.8; FIG. 10) and had no effect on acoustic startle alone (Wt ketamine, 798.6±106.3; Het ketamine, 862.7±149.5).

TABLE 3

Quantification of Fos expression in selected brain regions of female Wt vs. Het mice

| Forebrain | Female Wt (n = 11) | Female Het (n = 9) |
| --- | --- | --- |
| Piriform complex | 41.4 ± 3.7 | 31.8 ± 5.6# |
| Nucleus accumbens | 48.8 ± 3.4 | 25.5 ± 5.6** |
| Cingultate cortex | 28.3 ± 6.6 | 26.1 ± 5.7 |
| Retrosplenial cortex | 7.4 ± 1.9 | 1.4 ± 0.3* |
| Prelimbic cortex | 28.5 ± 6.3 | 10.3 ± 2.9* |
| Infralimbic cortex | 21.8 ± 5.5 | 10.8 ± 2.3* |

Data are displayed as mean ± SEM (*p < 0.05; **p < 0.01; #p < 0.15)

Our findings demonstrate marked effects of Mecp2 genotype on expression of the activity-dependent, immediate-early gene product Fos within specific forebrain and hindbrain networks, including many previously unrecognized sites of circuit dysfunction within the Mecp2 mutant brain. In view of the close spatial and temporal association between genotype effects on neural activity and Fos expression, our data indicate that loss of MeCP2 results in a stereotyped pattern of activity changes within a defined subset of functionally interrelated brain circuits that emerges during late postnatal development, coincident with the appearance of overt symptoms (Table 1).

Forebrain Circuitry and the Default Mode Network

Reduced expression of Fos in forebrain cortices is consistent with reports of hypoconnectivity in layer 5 cortical circuits in Mecp2 mutants. However, a particularly striking feature of the Fos map in Null mice is the marked reduction in labeling throughout the midline limbic network, including the medial prefrontal (mPFC), cingulate and retrosplenial cortices compared with Wt. This pattern of hypoactivity is significant because (1) these cortices are key nodes in the default mode network, a forebrain meta-circuit that also exhibits hypoactivity and/or reduced connectivity in human autism, and (2) the midline limbic cortices play a critical role in behavioral state regulation of autonomic homeostasis, which is abnormal in RTT.

Ketamine Rescue of Mutant Fos and PPI Phenotypes

Our finding that forebrain deficits in Fos expression in Nulls can be rescued by acute treatment with ketamine, even at subpsychotomimetic doses, illustrates that reduced Fos labeling reflects a reversible deficit in network activity, rather than an intrinsic inability to express Fos.

Circuits for Autonomic Homeostasis

Consistent with the pathophysiology of RTT, our data indicate circuit dysfunction in structures involved in both reflex and behavioral control of cardiorespiratory function, including the medulla (nTS), midbrain (PAG) and forebrain limbic cortices in Nulls.

Example 2

This Example evaluated the present study was undertaken to evaluate the ability of a small molecule, nonpeptide BDNF loop 2 domain mimetic, LM22A-4, which functions as a direct and specific partial agonist of TrkB, but not p'75, to increase TrkB activation and improve breathing in a mouse model of RTT. LM22A-4 was developed by in silico screening for mimetics of BDNF loop domains that selectively activate TrkB in vitro and in vivo and promote recovery of motor function in a rodent model of brain trauma. Using heterozygous female Mecp2 mutant mice, we show that daily treatment with LM22A-4 is well tolerated and rescues wild-type levels of TrkB phosphorylation and wild-type breathing frequency.

Materials and Methods

Animals

Mecp2tm1.1Jae mice were purchased and maintained on a mixed background (129Sv, C57BL/6, BALB/c) by crossing Mecp2$^{tm1.1Jae}$ heterozygous females (Mecp2$^{-/+}$, Het) with Mecp2$^{tm1.1Jae}$ wild-type males (Mecp2$^{+/p'}$). Experimental procedures were approved by the Institutional Animal Care and Use Committee at Case Western Reserve University.

BDNF Protein Measurements

BDNF concentrations were quantified by ELISA using the BDNF Emax Immunoassay System (Promega) according to the manufacturer's protocol. The sensitivity of this BDNF ELISA assay is ~1-3 pg BDNF/ml. Brain tissues and nodose ganglia were rapidly dissected and quick-frozen on dry-ice. Brain tissue samples were homogenized in 200 μl of RIPA buffer (containing, in mM: 50 Tris-HCl, 1% Nonidet P-40, 0.25% sodium deoxycholate, 150 NaCl, 1 EDTA, pH 7.4) containing a mixture of protease inhibitors (Roche), and centrifuged at 16,000×g for 15 min at 4° C. Nodose ganglia were homogenized in 100 μl of the same buffer and centrifuged at 14,000×g for 30 s at room temperature. The supernatant from each sample was collected and stored at −80° C. until further use. For brain tissue samples, an aliquot of the supernatant was used to determine total protein content using the Bradford technique and 300 μg of total protein were used for BDNF ELISA. For BDNF ELISA, the entire supernatant from each individual nodose ganglion was loaded.

TrkB, AKT, and ERK Phosphorylation Assays

The ratios of (1) phospho-TrkB$^{Y817}$/TrkB (full-length), phospho-ERK/ERK and phospho-AKT/AKT, (2) phospho-TrkB$^{Y817}$/actin, phospho-ERK/actin and phospho-AKT/actin, (3) TrkB (full-length)/actin, ERK/actin and AKT/actin and (4) TrkB (truncated)/actin were measured by Western blot using the ECL Chemiluminescence System (GE Healthcare). Site-specific rabbit monoclonal antiphospho-TrkB$^{Y817}$ antibody was obtained from Epitomics and rabbit polyclonal TrkB antibody was obtained from Millipore. Rabbit polyclonal ERK and AKT, mouse monoclonal phospho-ERK and phospho-AKT antibodies were obtained from Cell Signaling Technology. Tissues were homogenized in a lysis buffer (containing, in mM: 20 Tris, pH 8.0, 137 NaCl, 1% Igepal CA-630, 10% glycerol, 1 PMSF, 10 µg/ml aprotinin, 1 µg/ml leupeptin, 500 µM orthovanadate). Lysates were centrifuged at 14,000×g for 10 min, then the supernatant was collected and protein concentration was determined using the BCA Protein Assay Reagent (Pierce).

Spectrometric Analysis of LM22A-4 Levels in the Brain

The brain concentration of LM22A-4 (custom synthesized by Ricerca Biosciences, LLC) was evaluated in Het mice 1 h after a 50 mg/kg intraperitoneal dose using reverse-phase liquid chromatography with triple-quadrupole tandem mass spectrometric (LC-MS/MS) detection. Atenolol, a drug that does not cross the blood-brain barrier, was administered orally as a control to correct for contamination by blood present in the brain vascular space. Brainstem and forebrain samples were homogenized with a Virsonic 100 ultrasonic homogenizer and prepared for analysis using acetonitrile precipitation by combining one volume of sample with three volumes of acetonitrile. Samples were centrifuged and the resulting supernatant was sampled for analysis using a CTC Leap PAL autosampler (Leap Technologies) and two PerkinElmer series 200 micro pumps. Chromatography was performed at ambient temperature using a 50×2.0 mm inner diameter, 4 µm Synergi Polar-RP analytical column (Phenomenex). The aqueous mobile phase (A) was 4 mM ammonium formate, pH 3.5 and the organic mobile phase (B) was 10:90 (v/v) 4 mm ammonium formate, pH 3.5/acetonitrile. The analyte was eluted with a gradient which changed linearly from 0 to 100% B in 3 min at a flow rate of 300 µl/min. The total run time was 4.5 min and the injection volume was 10 µl. The analyte was detected on a Sciex API 3000 triple-quadrupole mass spectrometer equipped with a TurbolonSpray interface in the positive electrospray ionization mode (Applied Biosystems/MDS). The multiple reaction monitoring transitions and instrument settings were optimized for LM22A-4. Equipment operation, data acquisition, and data integration were performed using Analyst version 1.4.2. software (Applied Biosystems). The drug injections, tissue extraction and LCMS/MS analysis were performed by Absorption Systems.

Respiratory Function

Respiratory patterns were analyzed at 8, 10, and 12 weeks after birth in unrestrained mice using whole-body plethysmography as described previously. Measurements were taken from quiet breathing periods of at least 5 min total duration, and apneas were defined as pauses in breathing greater than two times the average breath duration calculated for each animal. LM22A-4 treatment. Wt and Het littermates were divided into 4 groups: Wt vehicle-treated (100 µl of 0.9% NaCl, i.p., b.i.d.), Wt drug treated (50 mg/kg LM22A-4 in 0.9% NaCl, i.p., b.i.d.), Het vehicle-treated (100 µl of 0.9% NaCl, i.p., b.i.d.), and Het drug-treated (50 mg/kg LM22A-4 in 0.9% NaCl, i.p., b.i.d.). Each mouse was treated from 8 to 13 weeks of age. Whole-body plethysmography was performed during week 12 and animals were subsequently killed and tissues harvested for TrkB Western blots and BDNF ELISA during week 13.

Statistical Analyses

Comparison of respiratory parameters between Wt and Het animals in the initial phenotyping experiments were performed using unpaired Student's t test. Comparisons among Wt vehicle-treated, Wt drug-treated, Het vehicle-treated, and Het drug-treated groups in the LM22A-4 trials, including plethysmography and Western blots were performed using one-way ANOVA with post hoc Least Significant Difference test (LSD) for intergroup comparisons. Results were considered significant if the p-value was <0.05. Data are presented as the mean±SEM.

Results

Development of Respiratory Dysfunction in Het Mice

The development of respiratory dysfunction in heterozygous Mecp2$^{tm1.1Jae}$ mice has not previously been described. Significant differences in breathing between Wt and Het mice first appeared between 8 and 10 weeks after birth (FIG. 8). At 10 weeks, Het mice exhibited an abnormally high breathing frequency associated with marked decreases in expiratory time ($T_e$) and total breath duration ($T_{tot}$) and a small but significant decrease in inspiratory time (Ti; FIG. 8A1-A4). Significant differences in respiratory frequency, $T_e$ and $T_{tot}$ (but not $T_1$) persisted at 12 weeks. The number of apneas in the Het population increased between 8 and 12 weeks of age (FIG. 8B1). This was due to a progressive increase in the proportion of Hets exhibiting significantly more apneas than Wt (20% at 8 weeks vs. 50% at 12 weeks).

BDNF Expression Deficits in the Brainstem of Het Mice

Mecp2$^{tm1.1Jae}$-null mice exhibit deficits in BDNF expression in structures critical for respiratory control, including the cranial sensory nodose ganglion (NG) and brainstem. To determine whether the development of respiratory dysfunction in Het mice is associated with changes in BDNF expression, we compared BDNF protein levels in these regions in Wt and Het mice at 8, 10, and 12 weeks of age (FIG. 9). BDNF levels in the Het NG were significantly below Wt at all 3 ages (FIG. 9A). Accordingly, we found reduced immunostaining for BDNF in the medullary nucleus tractus solitaries (nTS), the primary target of afferent projections from NG sensory neurons to the brainstem (FIG. 9D; 12 weeks of age). Despite this selective deficit within the Het nTS, differences in BDNF level between the Wt and Het medulla as a whole were only detectable by ELISA at 8 weeks of age (FIG. 9B). In the Het pons, the level of BDNF was normal at 8 weeks and fell below Wt values at 10 and 12 weeks (FIG. 9C).

Improved Respiratory Function Following LM22A-4 Treatment

In light of our finding that Het mice exhibit BDNF deficits in the nTS and pons, regions in which BDNF/TrkB signaling is important for respiratory control, we next sought to examine whether or not systemic administration of LM22A-4, a small molecule BDNF loop domain mimetic that acts as a selective TrkB agonist, could improve the Het breathing phenotype. To determine the brain penetrance of LM22A-4 following systemic administration, brainstem and forebrain samples were analyzed by LC MS/MS 1 h after a single intraperitoneal injection of 50 mg/kg LM22A-4 as described under Materials and Methods. These experiments demonstrated brain tissue concentrations (corrected for blood contamination) of 2.9 and 4.1 nM LM22A-4, respectively, which is well within the range at which LM22A-4 exhibits biological activity in assays of TrkB function. To evaluate the effects of systemic LM22A-4 administration on respiratory function, we used whole-body plethysmography to compare resting ventilation in 12-week-old Wt vehicle-treated, Wt drug-treated, Het vehicle-treated and Het drug-treated animals following 4 weeks of twice daily injections of LM22A-4 (50 mg/kg, i.p.) (FIG. 10A, B). In contrast to vehicle-treated Het controls, LM22A-4-treated Hets exhibited values of breathing frequency, $T_e$ and $T_{tot}$ that were not significantly different from those of Wt (FIG. 10A, B; pooled results of 4 independent experiments). The percentage of apneic animals was unaffected by drug treatment (data not shown), and there were no significant differences in respiratory function between vehicle- and drug-treated Wt mice. Moreover, drug treatment had no effect on body weight in either Wt or Het mice throughout the treatment period (FIG. 10C).

Figure 11:
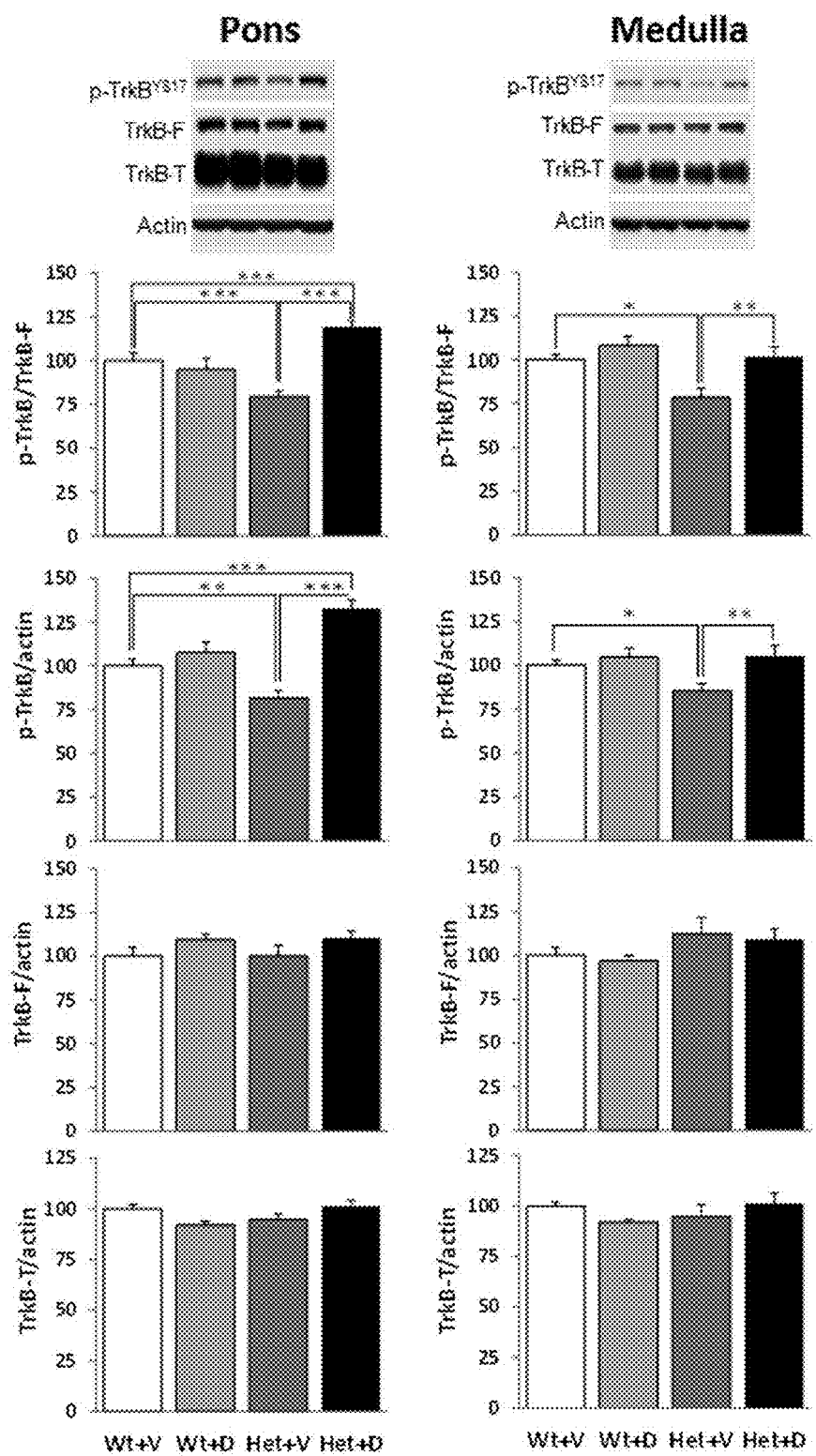
FIG. 11 illustrates TrkB phosphorylation deficits in Mecp2 Het mice are reversed by chronic treatment with LM22A-4. Top, Representative Western blots showing phosphorylated TrkB Y817 (p TrkB), full-length TrkB (TrkB-F), truncated TrkB (TrkB-T), and actin in medulla and pons samples from (left to right) Wt vehicle-treated, Wt drug-treated, Het vehicle-treated, and Het drug-treated mice. Graphs, Summary results showing the ratios of p-TrkB/TrkB-F, p-TrkB F/actin, TrkB-F/actin and TrkB-T/actin, respectively, in medulla and pons samples from all four treatment groups [open bars, Wt vehicle-treated (Wt+V); light gray bars, Wt drug-treated (Wt+D); dark gray bars, Het vehicle-treated (Het+V); black bars, Het drug-treated (Het+D)]. Results are expressed as the mean±SEM (medulla; Wt+V, n=9; Wt+D, n=3; Het+V, n=8; Het+D, n=13; pons; Wt+V, n=13; Wt+D, n=7; Het+V, n=11; Het+D, n=15). *$p<0.05$, $p<0.01$, *$p<0.001$, ANOVA I with post hoc LSD test.
Figure 12:
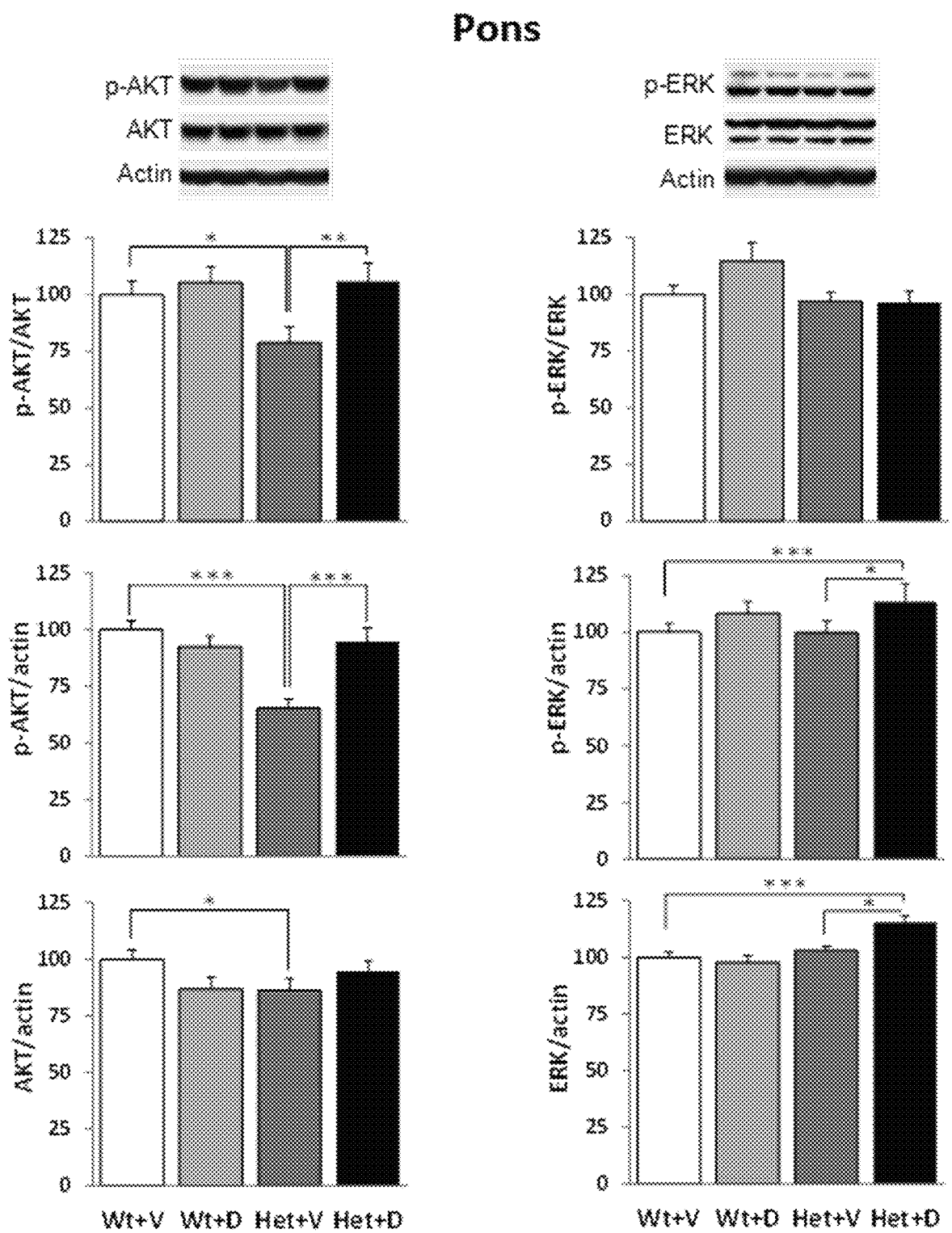
FIG. 12 illustrates AKT phosphorylation deficits in the pons of Mecp2 Het mice are reversed by chronic treatment with LM22A-4. Top, Representative Western blots showing p-AKT, total AKT (AKT), p-ERK, total ERK (ERK), and actin in pons samples from (left to right in each blot) Wt+V, Wt+D, Het+V, and Het+D mice. Graphs, Summary results showing the ratios of p-AKT/AKT, p-ERK/ERK, p-AKT/actin, p-ERK/actin, AKT/actin and ERK/actin in pons samples from all four treatment groups (open bars, Wt+V; light gray bars, Wt D; dark gray bars, Het+V; black bars, Het+D). Results are expressed as the mean±SEM (Wt+V, n=13; Wt+D, n=7; Het+V, n=11; Het+D, n=14). *$p<0.05$, $p<0.01$, *$p<0.001$, ANOVA I with post hoc LSD test.
Figure 13:
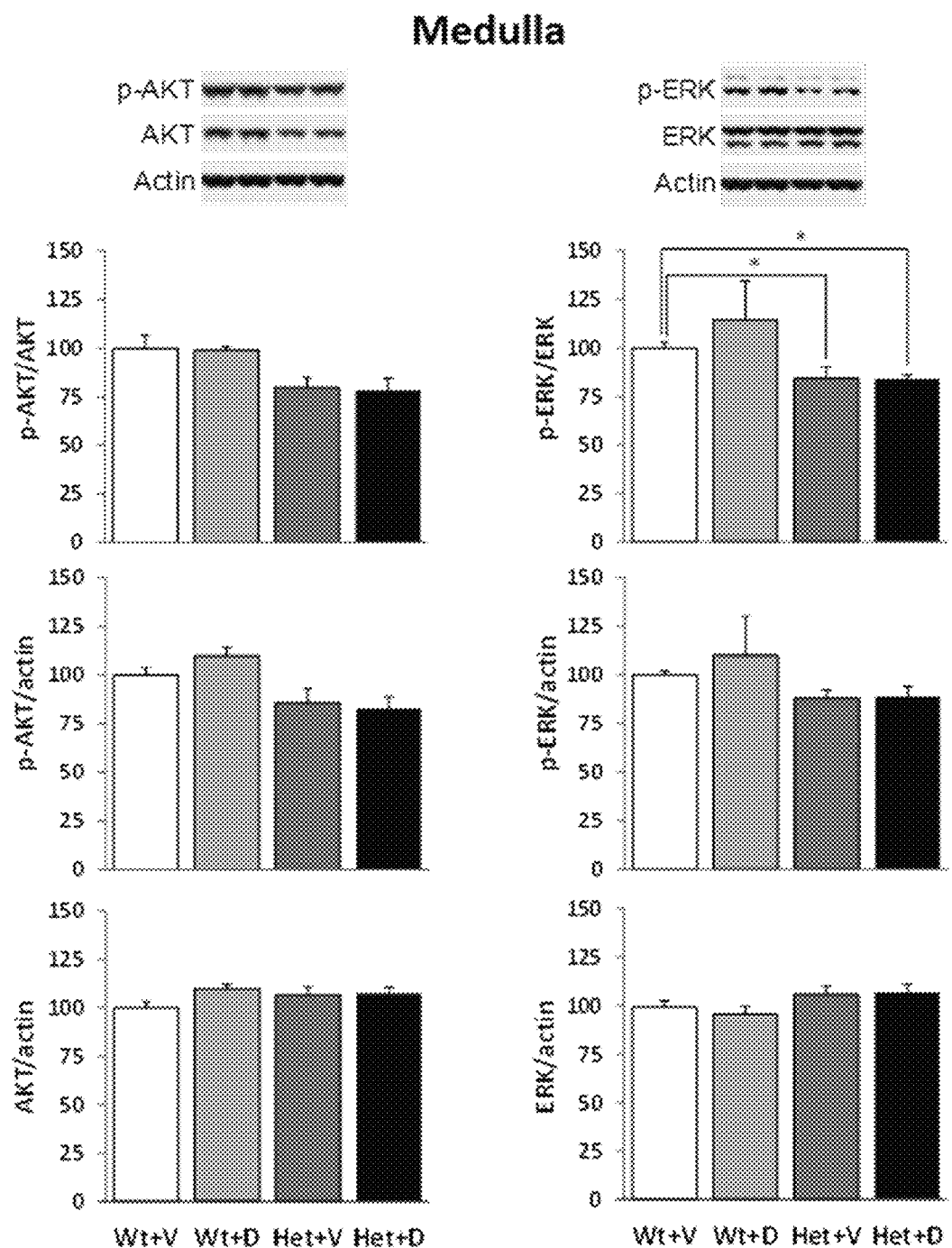
FIG. 13 illustrates AKT and ERK phosphorylation in the medulla. Top, Representative Western blots showing p-AKT, total AKT (AKT), p-ERK, total ERK (ERK) and actin in medulla samples from (left to right in each blot) Wt+V, Wt+D, Het+V, and Het+D mice. Graphs, Summary results showing the ratios of p-AKT/AKT, p-ERK/ERK, p-AKT/actin, p-ERK/actin, AKT/actin and ERK/actin in medulla samples from all four treatment groups (open bars, Wt+V; light gray bars, Wt+D; dark gray bars, Het+V; black bars, Het+D). Results are expressed as the mean SEM (Wt+V, n=9; Wt+D, n=3; Het+V, n=8; Het+D, n=13). *$p<0.05$, $p<0.01$, *$p<0.001$, ANOVA I with post hoc LSD test.

LM22A-4 Treatment Reverses TrkB Phosphorylation Deficits in the Brainstem of Het Mice We next sought to determine whether or not improved respiratory function in LM22A-4-treated Hets is associated with increased TrkB signaling in the brainstem. To address this issue, we used Western blots to compare the ratio of phosphorylated TrkB to total full-length TrkB (p-TrkB$^{Y817}$/TrkB) in 13-week-old Wt vehicle-treated, Wt drug-treated, Het vehicle-treated, and Het drug-treated animals following 5 weeks of systemic treatment with LM22A-4 (50 mg/kg, i.p., b.i.d.) (FIG. 11). To control for possible changes in total TrkB levels between Wt and Het samples, or with LM22A-4 treatment, we also compared the ratios of p-TrkB$^{Y817}$, total full-length TrkB and total truncated TrkB to actin (p-TrkBY817/actin, TrkB/actin, TrkB-T/actin, respectively). Pons and medulla samples from vehicle-treated (control) Hets exhibited significant decreases in p-TrkBY817/TrkB and p-TrkBY817/actin compared with vehicle treated (control) Wt animals with no change in the levels of total full-length TrkB or truncated TrkB. These deficits in TrkB phosphorylation in Het mice were completely reversed by treatment with LM22A-4 (FIG. 11). In fact, drug-treated Hets showed significantly higher levels of p-TrkB/TrkB and p-TrkB/actin than wild-type controls in the pons. We also examined whether or not genotype and drug effects on TrkB phosphorylation were reflected in changes in phosphorylation of the serine/threonine protein kinase AKT (p-AKT) and extracellular signal regulated kinase ERK/MAPK (p-ERK), key downstream mediators of the biological effects of TrkB activation. These experiments demonstrated significant decreases in p-AKT/AKT and p-AKT/actin in the pons of Het mice compared with Wt controls that were reversed by LM22A-4 treatment, with no change in total AKT levels (FIG. 12). In contrast, there was no significant effect of genotype or drug treatment on the level of p-ERK/ERK in pons samples from Wt and Het mice. In the medulla, although p-AKT/AKT and p-AKT/actin tended to be lower in Het mice compared with Wt, these trends were not statistically significant. p-ERK/ERK in the medulla was significantly lower in Het animals compared with Wt controls in both vehicle- and drug treated animals (FIG. 13).

The present finding that pharmacologic activation of TrkB in Mecp2 Het mice eliminates respiratory tachypnea supports the role of BDNF/TrkB signaling deficits in respiratory dysfunction in RTT and provides proof-of-concept for the therapeutic potential of TrkB agonists to improve this and other aspects of the disease. In summary, our data demonstrate the ability of a BDNF loop domain mimetic to enhance TrkB activation and restore wildtype respiratory frequency in Mecp2 Het mice. These findings provide validation of TrkB as a therapeutic target in mouse models of RTT and indicate that BDNF loop domain mimetics can be effective at overcoming functional deficits associated with reduced BDNF expression.

Example 3

This Example evaluated a ketamine dosing regimen for the treatment of Rett syndrome. We show that treatment of RTT mice with a low, sub-anesthetic dose of the NMDA receptor (NMDAR) antagonist ketamine acutely reverses brain activity deficits in RTT mice and significantly improves prepulse inhibition of acoustic startle, a measure of cortical function. These effects are consistent with the ability of ketamine to increase activity in cortical pyramidal cells by selectively inhibiting cortical inhibitory interneurons. We further found that treatment of RTT mice with a very low dose of ketamine(3 mg/kg), once every 3 days, for two weeks results in complete elimination of apneic breathing, a core feature of RTT, 24 hours after the last ketamine injection (FIG. 14).

The persistence of apnea reversal for 24 hours is highly significant because the half-life of ketamine is extremely short (less than 1 hour). Therefore, our data suggest that repeated intermittent dosing with ketamine results in sustained alteration in the underlying substrate of the disease rather than simply symptomatic relief. Moreover, the ability to use a very low, sub-anesthetic dose of ketamine in this treatment paradigm should reduce, and possibly eliminate the risk of potential adverse effects associated with higher doses of this drug.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. An intermittent dosing regimen for treating Rett syndrome (RTT) in a subject, the intermittent dosing regimen comprising:
   administering subanesthetic doses of ketamine at a first dosing interval, the first dosing interval effective to alleviate at least one neurological symptom associated with RTT, then withholding dosing for about 1 to about 12 months, and then resuming administration of subanesthetic doses of ketamine at a second dosing interval upon recurrence of the at least one neurological symptom, the second dosing interval effective to alleviate the at least one neurological symptom.

2. The method of claim 1, wherein the ketamine is administered in an amount effective to ameliorate biochemical and functional abnormalities associated with loss-of-function mutations of the gene encoding methyl-CpG binding protein 2 (MeCP2) in the subject.

3. The method of claim 2, wherein the ketamine is administered at the subanesthetic dose of less than 10 mg/kg.

4. The method of claim 1, further comprising administering to the subject a therapeutically effective amount of a TrkB agonist, an ampakine, and/or a GABAR agonist.

5. The method of claim 4, the ampakine comprising at least one of 1-(1,4-benzodioxan-6-ylcarbonyl)piperidine, 1-(quinoxalin-6-ylcarbonyl)piperidine, 2H,3H,6aH-pyrrolidino[2",1"-3',2"]1,3-oxazino[6',5'-5,4]benzo[e]1,4-di-oxan-10-one or a pharmaceutically effective salt thereof.

6. The method of claim 1, wherein the at least one neurological symptom associated with RTT is selected from the group consisting of a motor, respiratory and autonomic dysfunction.

7. The method of claim 1, wherein the at least one neurological symptom associated with RTT is apneic breathing.

8. The method of claim 1, wherein each subanesthetic dose of ketamine administered to the subject during the first dosing interval and the second dosing interval is administered to the subject in the form of a single individual dose unit, wherein the time between administration of each single individual dose unit is at least 24 hours.

\* \* \* \* \*